(12) United States Patent
Junqua et al.

(10) Patent No.: US 9,335,904 B2
(45) Date of Patent: May 10, 2016

(54) CONTEXT DEPENDENT APPLICATION/EVENT ACTIVATION FOR PEOPLE WITH VARIOUS COGNITIVE ABILITY LEVELS

(71) Applicant: Panasonic Corporation of North America, Secaucus, NJ (US)

(72) Inventors: Jean-Claude Junqua, Saratoga, CA (US); Ricardo Teixeira, Cupertino, CA (US); Mike Wang, San Jose, CA (US); David Koo, Exeter, CA (US)

(73) Assignee: Panasonic Corporation of North America, Newark, NJ (US)

( * ) Notice: Subject to any disclaimer, the term of this patent is extended or adjusted under 35 U.S.C. 154(b) by 205 days.

(21) Appl. No.: 14/096,475

(22) Filed: Dec. 4, 2013

(65) Prior Publication Data

US 2014/0164945 A1  Jun. 12, 2014

Related U.S. Application Data

(63) Continuation-in-part of application No. 13/729,960, filed on Dec. 28, 2012, now Pat. No. 9,208,661, and a continuation-in-part of application No. 13/730,327, filed on Dec. 28, 2012, now Pat. No. 8,803,690.

(60) Provisional application No. 61/631,500, filed on Jan. 6, 2012.

(51) Int. Cl.
*G06F 17/30* (2006.01)
*G06F 3/0484* (2013.01)
(Continued)

(52) U.S. Cl.
CPC .......... *G06F 3/0484* (2013.01); *G06F 19/3412* (2013.01); *G06F 19/3418* (2013.01); *G06F 19/3431* (2013.01); *G06F 19/3456* (2013.01); *H04L 41/22* (2013.01); *G08B 21/0423* (2013.01)

(58) Field of Classification Search
USPC .............. 340/573.1, 309.4, 539.12, 457, 522, 340/691.3; 707/796; 715/747
See application file for complete search history.

(56) References Cited

U.S. PATENT DOCUMENTS 6,442,573 B1    8/2002  Schiller et al.
7,058,895 B2 *  6/2006  Kautto-Koivula .... G06F 3/0481
                                                              709/229

(Continued)

OTHER PUBLICATIONS

Bulucea, Carmen Aurora, et al., "Real Time Medical Telemonitoring of Sustainable Health Care Measuring Devices," Proceedings of the 8th WSEAS International Conference on Artificial Intelligence, Knowledge Engineering and Data Bases, Cambridge, United Kingdom, Feb. 21-23, 2009, pp. 202-207.

*Primary Examiner* — Hung T Vy
(74) *Attorney, Agent, or Firm* — Harness, Dickey & Pierce, P.L.C.

(57) ABSTRACT

The patient device, designed for use by patients of reduced cognitive or physical ability, integrates with the network-based portal, designed for use by family members or nursing staff to customize the user experience of the patient. Using the portal the family member pushes user interface customizations as well as content and applications to be run on the patient device. The family member can also control the patient device remotely via the portal. The patient device collects usage data on the set of customizable interface components, and on the pushed content and applications. These data are sent as feedback to the portal, allowing the portal to show the family member which user interface features, content and applications are being used and which are not. Aggregate data collected via the portal generate ranking metrics used to aid in user interface feature selection.

14 Claims, 39 Drawing Sheets

(51) Int. Cl.
*H04L 12/24* (2006.01)
*G06F 19/00* (2011.01)
*G08B 21/04* (2006.01)

(56) References Cited

U.S. PATENT DOCUMENTS

| | | |
|---|---|---|
| 7,076,737 B2 | 7/2006 | Abbott et al. |
| 7,107,346 B2 | 9/2006 | Boyd |
| 7,224,777 B1 | 5/2007 | Tannenbaum |
| 2003/0036683 A1* | 2/2003 | Kehr .................... G06F 19/325 600/300 |
| 2006/0066448 A1 | 3/2006 | Berisford et al. |
| 2007/0197881 A1 | 8/2007 | Wolf et al. |
| 2007/0234290 A1* | 10/2007 | Ronen ..................... G06F 8/36 717/120 |
| 2009/0249359 A1* | 10/2009 | Caunter ................ G06F 9/4448 719/315 |
| 2011/0070835 A1 | 3/2011 | Borras et al. |
| 2011/0221568 A1 | 9/2011 | Giobbi |
| 2011/0227739 A1 | 9/2011 | Gilham et al. |
| 2012/0011570 A1 | 1/2012 | Griffin |

* cited by examiner

Mary
Today is
Monday

October 10, 2011 8:50 AM Morning

320

Morning Pills

Lunch with Joe
Meet in Lobby
In about 3 Hours

Noon
12:00

Alice will Visit
Tomorrow

Afternoon
3:00PM

Figure 3

| Event Title & Notes | After Event Starts | Event Start | Event End | Starts Showing | Entered By & Edit Options |
|---|---|---|---|---|---|
| Morning Pills | Did you take Pills? | Mon - Dec 12, 2011<br>9:00 am<br>'Please take your pills'<br>30 min. before | 1 Hr. 57 Min.<br>10:57 am<br>Repeat Daily | 30 Min. before event<br>Will show OK Button<br>30 Min. before event<br>Alert Enabled | gary johnson |
| Dinner with Jerry | | Tue - Dec 13, 2011<br>6:00 pm<br>No Music | 2 Hrs<br>8:00 pm | Now Showing | Jerry Lowe<br>*Edit*  ← 1300 |
| Your Birthday Soon | Happy Birthday | Wed - Dec 14, 2011<br>All Day<br>No Music | Repeat Yearly | Now Showing | gary johnson  ← 1310 |
| Lunch with Joe<br>Meet in Lobby | | Fri - Dec 16, 2011<br>12:00 pm<br>Soft Piano<br>20 Min Before | 2 Hrs<br>2:00 pm | Dec 15, 2011<br>Day Before Event | gary johnson |
| Visit Alice<br>Joe will pick you up | At Alice's | Sat - Dec 17, 2011<br>11:30 am<br>Soft Piano<br>20 min. before | Tue - Dec 20, 2011<br>6:00 pm | Now Showing | gary johnson |
| Christmas is coming | Merry Christmas | Sun - Dec 25, 2011<br>All Day<br>No Music | Repeat Yearly | Dec 21, 2011<br>4 Days Before Event | Valley Home<br>Sacramento<br>Group  ← 1320 |

Figure 13

1800 → *Add Preset*

| BACK See More Events ▮ 1 - 1 / 1 | | | | | |
|---|---|---|---|---|---|
| Event Title & Notes | After Event Starts | Event Start | Event End | Starts Showing | Entered By & Edit Options |
| Dentist Appointment | | Date TBD 11:00 am Soft Piano 20 Min. before | 2 Hrs 1:00 pm | 2 Days Before Event | gary johnson *Edit* |
| Christmas is coming | Merry Christmas | Sun - Dec 25, 2011 All Day No Music | Repeat Yearly | Dec 21, 2011 4 Days Before Event | Admin |
| New Years is coming | Happy New Years | Sun - Jan 1, 2012 All Day No Music | Repeat Yearly | Dec 28, 2011 4 Days Before Event | Admin |
| Memorial Day is soon | Memorial Day | Mon - May 28, 2012 All Day No Music | Yearly: Same Month, Week, Day of Week | May 22, 2012 2 Days Before Event | Admin |

Display

SETTINGS

Display Features
You can pick when the display goes into different modes. The different modes will determine the brightness of the screen. You Pick if you want sounds to be played during those modes.

| | | | | |
|---|---|---|---|---|
| Day mode start | 01:00 AM ▶ | | Day sound | Enabled ▶ |
| Night mode start | 08:00 PM ▶ | | Night sound | Enabled ▶ |
| Sleep mode start | 10:00 PM ▶ | | Detect sound | Disabled ▶ |
| Screen saver | Disabled ▶ | | | |

Accessibility Features
Text-to-speech allows the display to read out loud activities and messages in absolute or relative time when they are touched on the display. You can also make events and messages easier to read by increasing the zoom level.

| | | | | |
|---|---|---|---|---|
| Text-to-speech | Enabled ▶ | | Speech type | Absolute Time ▶ |
| Font zoom level | 5 (Largest) ▶ | | Return to calendar | When this is a NOW acti▶ |
| Vertical scroll | Enabled ▷ | | | |

Figure 38

Display

Name [          ] [Choose File] No file chosen [Upload]
Max. size 10 MB

Name [                              ]
06_bobby_mc_ferrin.mp3                     [Delete]

Video

Name [          ] [Choose File] No file chosen [Upload]
Max. size 100 MB

Name [                              ] Ready to display
IMG_0202.MOV                              [Delete]

Figure 40

SKYPE

| Skype App | Enabled ▶ | | |
|---|---|---|---|
| Username 1 | David.koo8 | Fullname 1 | David Koo |
| Username 2 | mxbluei3oi | Fullname 2 | Mike Wang |
| Username 3 | ricardohteixeira | Fullname 3 | Richardo Teixeira |
| Username 4 | psvlsurvey | Fullname 4 | Demo |
| Username 5 | Username | Fullname 5 | Fullname |
| Username 6 | Username | Fullname 6 | Fullname |

Figure 41

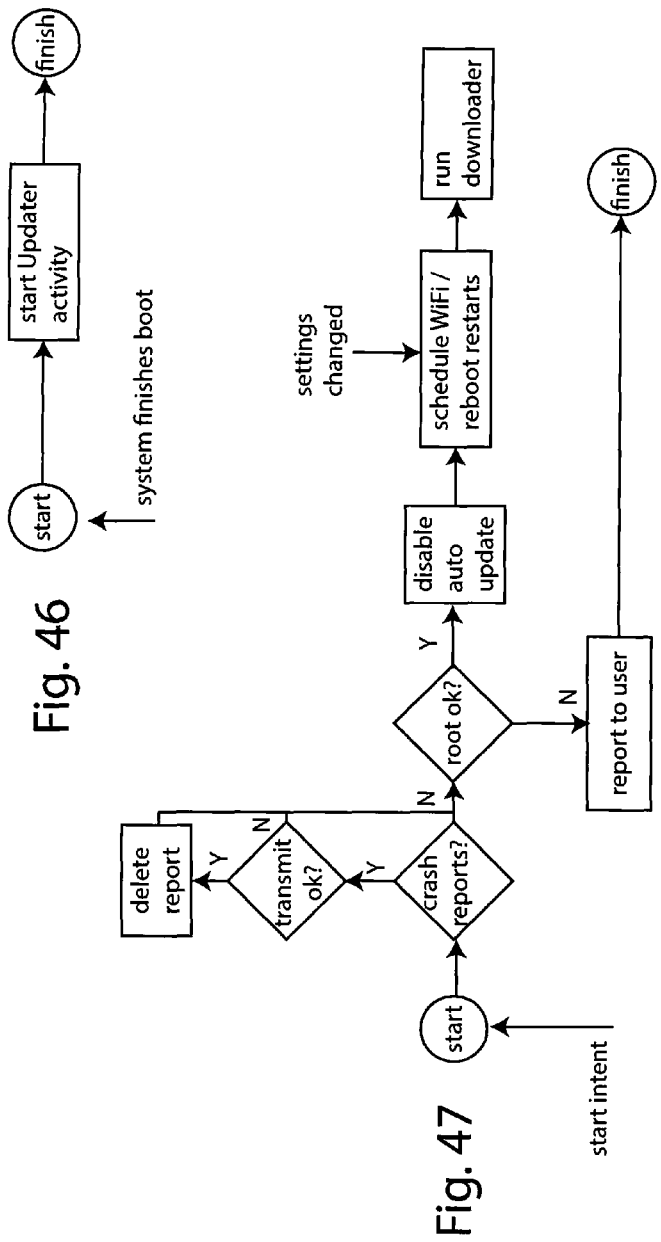
Fig. 46
Fig. 47
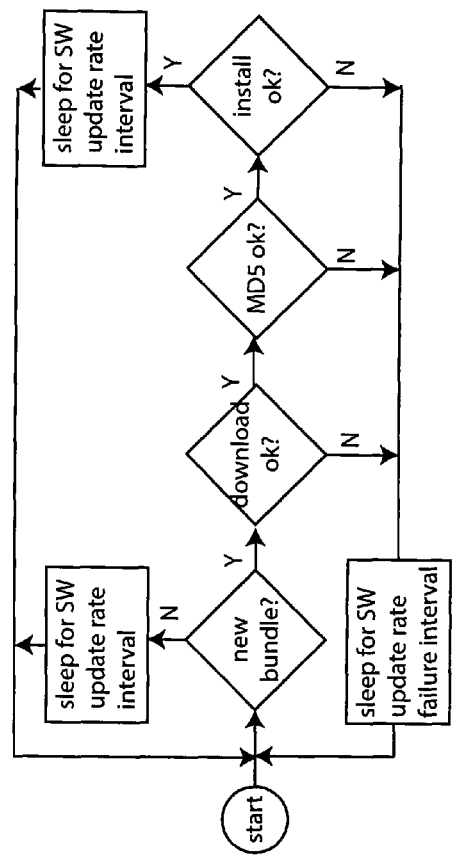
Fig. 48

CONTEXT DEPENDENT
APPLICATION/EVENT ACTIVATION FOR
PEOPLE WITH VARIOUS COGNITIVE
ABILITY LEVELS

CROSS-REFERENCE TO RELATED
APPLICATIONS

This is a continuation-in-part of U.S. patent application Ser. Nos. 13/729,960 and 13/730,327, both filed on Dec. 28, 2012, both of which claim the benefit of U.S. provisional application No. 61/631,500, filed on Jan. 6, 2012. The entire disclosures of each of the above applications are incorporated herein by reference.

TECHNICAL FIELD

This disclosure relates to a computer-implemented system for assisting persons of reduced cognitive or physical ability to manage upcoming events and to stay in touch with loved ones.

BACKGROUND

People with early to moderate Alzheimer's disease or dementia suffer from both memory loss and the inability to operate complex devices. These people are often anxious about missing events or activities, or forgetting other time-based issues. Consequently, these people often write copious notes to themselves. The accumulation of notes results in another form of confusion because they forget which notes matter and when they matter.

With the growing popularity of portable devices, such as smartphones and tablet devices, one might assume that these devices might be pressed into service, as an aid to helping persons with reduced cognitive or physical ability remember important events. However, this is by no means as simple as it might at first blush appear. Persons with reduced cognitive ability may have extreme difficulty interacting with these portable devices. First, on account of the reduced cognitive ability, the person may not understand how to use a particular user interface feature or application running on the device. Second, as is frequently the case, the person may also have physical disabilities that make it difficult to manipulate user interface features on the device.

To make matters worse, there is no one-size-fits-all solution when it comes to designing a user interface that is well-suited to a particular person's level of cognitive or physical ability. Moreover, as is unfortunately the case, a person's abilities may also degrade over time. Thus a perfectly adapted user interface one day may no longer fit the person's needs six months later.

Family members are anxious to help, and yet they too can struggle with user interface complexities. Although family members may think they have delivered their aging loved one a helpful portable device, there is truly little way of knowing if the device actually helps at all. Quite too often, the portable device will sit unused in the elderly person's room because it is perceived by that person as too foreign and complex to be useful. When a family member ultimately learns that the device is not being used, he or she has no effective way to correct the situation, as the typical family member is by no means an expert in user interface design for the cognitively or physically impaired.

SUMMARY

This section provides a general summary of the disclosure, and is not a comprehensive disclosure of its full scope or all of its features.

The present disclosure provides a solution to the aforementioned problems in the form of an integrated patient device (e.g., portable device) and network-based portal combination. The patient device is designed for use by patients of reduced cognitive or physical ability. The patient device integrates with a network-based portal, designed for use by family members or nursing staff to customize the user experience of the patient. Using the portal the family member or nursing staff person pushes user interface customizations as well as content and applications to be run on the patient device. The family member or nursing staff can also control the patient device remotely via the portal.

The patient device collects usage data on the set of customizable interface components, and on the pushed content and applications. These data are sent as feedback to the portal, allowing the portal to show the family member or nursing staff which user interface features, content and applications are being used and which are not. Aggregate data collected via the portal generate ranking metrics used to aid in user interface feature selection.

The portal includes an integrated database or kit of user interface (UI) components from which the family member or nursing staff may select to construct a customized user interface and user experience specially designed for a particular patient. Stored within the integrated database, each UI component has at least one associated cognitive ability or physical ability metric that ranks the understandability and usability of that UI component for that particular patient.

When the family member wishes to customize the user interface of a particular application, or even the global operation of the patient device itself, he or she can compare these cognitive ability metrics and physical ability metrics of each UI component and select the ones that will best work for the specific patient.

As the patient uses the device, actual usage data are collected on each UI component used, and when used. From these data, a feedback signal is sent to the portal, allowing the portal computer to factor this usage data into determining what usage metric to apply to the various UI components actually used (or not used) by the patient. The portal computer is also programmed to share usage statistics with a cloud-based aggregation computer that generates aggregate complexity statistics and metrics representing an entire population of patents who are using the patient device. Preferably these usage statistics are shared with the cloud-based aggregation computer without revealing any patient-specific information to ensure privacy of the patient is protected.

If desired, the integrated database may also be configured to store similar suitability metrics in association with various different selections of content pushed to the device. In this regard, if a long 60-minute video is pushed to the device and the patient only watches two minutes, that usage data reflects the suitability level of the content for this particular patient is low and a low suitability metric is thus assigned to that content. This low metric shows the family member or nursing staff that the content selected to be pushed to the patient device may be too "difficult" or uninteresting to the patient.

In a similar manner the integrated database may also be configured to store similar suitability metrics in association with various different selections of applications pushed to the device to be run on the device. For example, if an instant messaging application is pushed to the patient device, but usage metrics indicate that this application is never used, a low suitability metric is assigned. This low metric shows the family member or nursing staff that the instant messaging application selected to be pushed to the patient device may be too "difficult" or uninteresting for this particular patient.

Therefore, according to one aspect, the disclosure describes a computer-implemented system for assisting persons of reduced cognitive or physical ability comprising. The system includes a patient device having a display, a processor coupled to the display, and a communication port through which it communicates with a portal computer. The processor of the patient device is programmed to provide feedback data to the portal computer regarding use by the patient of the selected user interface component pushed to the patient device.

The portal computer has a processor and associated memory storing a plurality of user interface components according to a predefined data structure that associates an ability metric with each user interface component. The portal computer is programmed to present the plurality of user interface components to a first user of the portal computer in a presentation arrangement based on the ability metric. The portal computer is further programmed to allow the first user to select from the arranged presentation of user interface components at least one interface component and then to push said selected user interface component to the patient device.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

FIG. 3 shows an example messaging seen on a display device after a reminder was acknowledged.

FIG. 13 illustrates an example user interface as seen by a regular user for reviewing all active reminders and messages for a particular display device.

FIG. 18 illustrates an example user interface showing existing preset reminders.

FIG. 38 is an exemplary display screen generated by the portal computer with which settings of the patient device are customized.

FIG. 40 is an exemplary display screen generated by the portal computer with which settings of applications (e.g., music and video applications) for the patient device are customized to add selected digital content.

FIG. 41 is an exemplary display screen generated by the portal computer with which settings of an audio-video chat application (e.g., Skype) for the patient device are customized from the portal computer.

FIG. 46 illustrates the software architecture of the portal device, showing the updater broadcast receiver.

FIG. 47 illustrates the software architecture of the portal device, showing the wrapper activity start.

FIG. 48 illustrates the software architecture of the portal device, showing the wrapper activity downloader.

DESCRIPTION OF PREFERRED EMBODIMENTS

Overview

Figure 1:
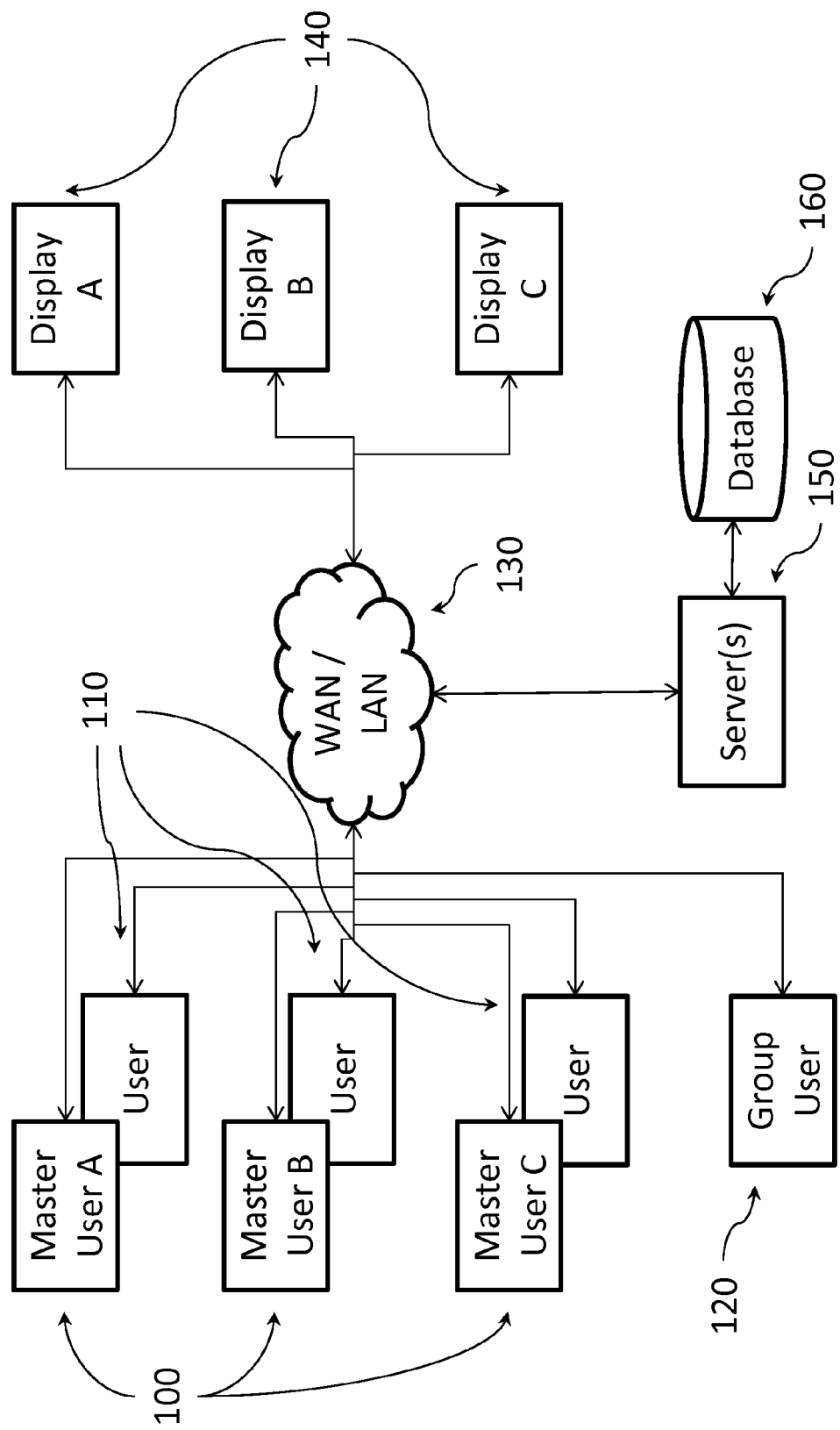
FIG. 1 shows a general system architecture showing users, display devices, a server-based system, and a network.

The disclosed system allows people (e.g., friends, family, administrators) in a remote or local location to create reminder messages that will show at the appropriate times and with appropriate messaging on a relatively simple display device. This display device need not have any controls that the viewer interacts with, so a person with Alzheimer's does not need to learn how to operate it. The only interaction that this display device needs happens during a one-time initial setup step, and optional reminder acknowledgements that require only the press of one button.

The system works via a network, such as the Internet and/or local area network (LAN). People (friends, family, administrators) interface to the system via any modern browser. The system, in turn, interacts with the display device via the network.

The system accommodates multiple display devices and multiple accounts. More than one person can be given the ability to create a reminder message. A master account(s) is also given the ability to edit messages from other accounts, as well as other privileges. For situations such as an assisted living home, a group administrator account can send messages to groups of display devices, or to just one display device. However, accounts that are associated directly with a particular display device can hide such group messages if needed.

Account holders associated with a particular display device can see each other's reminders, including group messages, so that friends and family can be informed about the planned or current activities of the person for whom the reminders are intended. However, group account holders can only see their own group messages, unless permission is granted otherwise, to preserve privacy.

Messaging can be set up in advance, and made to appear at the appropriate times relative to the event they refer to. The content and level of detail of the messaging, including audio, changes according to how close it is to the event in question. Once the event starts, messaging continues until the event is finished, and the content of this messaging changes according to when it is relative to the end of the event.

Reminders can be programmed to automatically repeat at specified intervals, from daily to yearly, to accommodate a variety of situations and events.

Reminders can optionally require that an acknowledgement by the viewer take place. Multiple acknowledgement requests can be active at one time. If such a reminder is not acknowledged, remote users (friends, family, and administrators) can check the status and/or receive an alert via a short message service or email.

Preset reminders exist to help save typing. Account holders can use system-defined preset messages or create their own for future use. Preset messages can be customized by the account user.

Messages can also be "instant messages" that are not tied to any particular event. Such instant messages appear relatively quickly and do not require any action by the viewer to see.

To avoid potential failure situations, such as equipment failure, loss of power or communications, the system can monitor the health of each display device and alert the appropriate account holders and/or administrators of such a failure.

In one aspect the system focuses on providing hybrid care assistance dependent on the cognitive abilities of a patient, ranging from full third-party control to shared control to an independently functioning patient, in an automatic and natural manner. Third-party control of the system can be local or remote. Further, the system itself will adapt the level of interaction provided to the patient based on further improvement or decline in cognitive ability.

Thus, the system works to automatically and naturally adapt the triggering of events (e.g., launching applications/events on a display) based on the following core functionalities:

A. Arm/set the event/App by a third party (e.g., family member)
B. Estimation of an event context. The context can take several forms (medical, situational, etc.) depending on the event to be triggered
C. Launch of the event based on matching the context with the present situation and the person's cognitive ability In addition to the above core functionalities, the system also offers a number of additional advantages, including the following:

An application can be triggered automatically in a non-intrusive way (e.g., audio message when the patient is not sleeping)
The launch and the interaction with the application can be customized to the patient's cognitive ability
The patient can enjoy a number of services (e.g., see family pictures, video conference or reminders, listen to music) without having to know how to launch the application/event
Personal preferences of the patient can be taken into account to customize the system's services
The solution includes implicit interaction (from the patient's point of view) with explicit interaction (from the third party who arms the event/application point of view)
Our solution is about when to launch an application/event, and how to launch an application/event

DETAILED DESCRIPTION

Example embodiments will now be described more fully with reference to the accompanying drawings.

FIG. 1 illustrates the general system architecture, showing a set of different types of remote users, a server system and a set of display devices (or simply "display" or "displays" in subsequent descriptions). Each User 100, 110 interacts with the system via the network 130, which can be a combination of wide area (such as the Internet) or local area networks.

Each user is associated with a particular display 140. In the illustration, Master User A 100 and a related Normal User 110 interact with Display A. In turn, there is a separate set of users associated with display B, etc.

User accounts center around the display. There is at least one Master User 100 associated with each display. The Master User has ultimate control over how the display looks. The Master User can do the following:

Create new event reminders and messages

Edit event reminders and messages that he or she created or those created by any other Master or Normal user that belongs to the managed display Create new Master or Normal users for the display Control whether or not Group events are enabled on the display (see Group users)

Hide or Show a specific Group event reminder that was sent to the display. Hiding a Group event reminder might be necessary if this event is in conflict with another event that the Master (or Normal) user has planned.

See event reminders and messages that anyone has created for the display

Create and edit preset event reminders that others can also use

Change the display's details, such as names, location and time zone

Change his or her own user details, such as names, username, email address and password Normal or regular Users 110 can place messages on this display, but have fewer privileges:

Edit event reminders and messages that they created

Hide or Show a specific Group event reminder that was sent to the display

See event reminders and messages that anyone has created for the display

Create and edit preset event reminders that others can also use

Change their own user details, such as names, username, email address and password Group users 120 can be associated with more than one display. FIG. 1 only shows one group user to illustrate a situation where there are three displays (A, B, C) at a particular facility that this group user has access to. Master Users can do the following:

Invite a Master user to join this Group by sending them an email invitation. To send such an invitation, the Group user will need to ask for the Master user's 'username'. The Master user that receives the email invitation to join the Group must then click on a link to accept the invitation. The Master User still reserves the right to disable any or all Group events from showing on their display.

Create and edit Group event reminders and instant messages that go to all displays enabled to accept group events from this Group user Specify that an event reminder or instant message go to just one display (instead of all displays)

Group users cannot see the event reminders and messages that have been created by Master and Normal users for any particular display, unless permission is given to expose a particular item Change their own user details, such as names, username, email address and password The Server 150 manages the system, including the access to the system by each of the users and the updating of each of the displays. Again, FIG. 1 only shows a subset of what is possible because one server 150 can manage a number of set of users and displays scattered around the world. Databases 160 store all of the information on all users, displays and messages. Sensitive information, such as passwords and email addresses, are kept encrypted.

In a typical operation, a user interacts via a web browser or dedicated application with the system to create a reminder. This reminder is stored in the database and the server then determines which reminders should go to each particular display at the appropriate times. Users can view the status of all reminders and messages, including making edits and hiding messages as appropriate.

The displays merely display the messages that they are sent. Optionally, they can do a small amount of management of these messages to minimize the amount of communications needed during operation. Optionally, these displays may provide a simple way (e.g., touch the display, verbally, etc.) for a viewer to respond to a message, if requested, and this response is sent back to the server.

Figure 2:
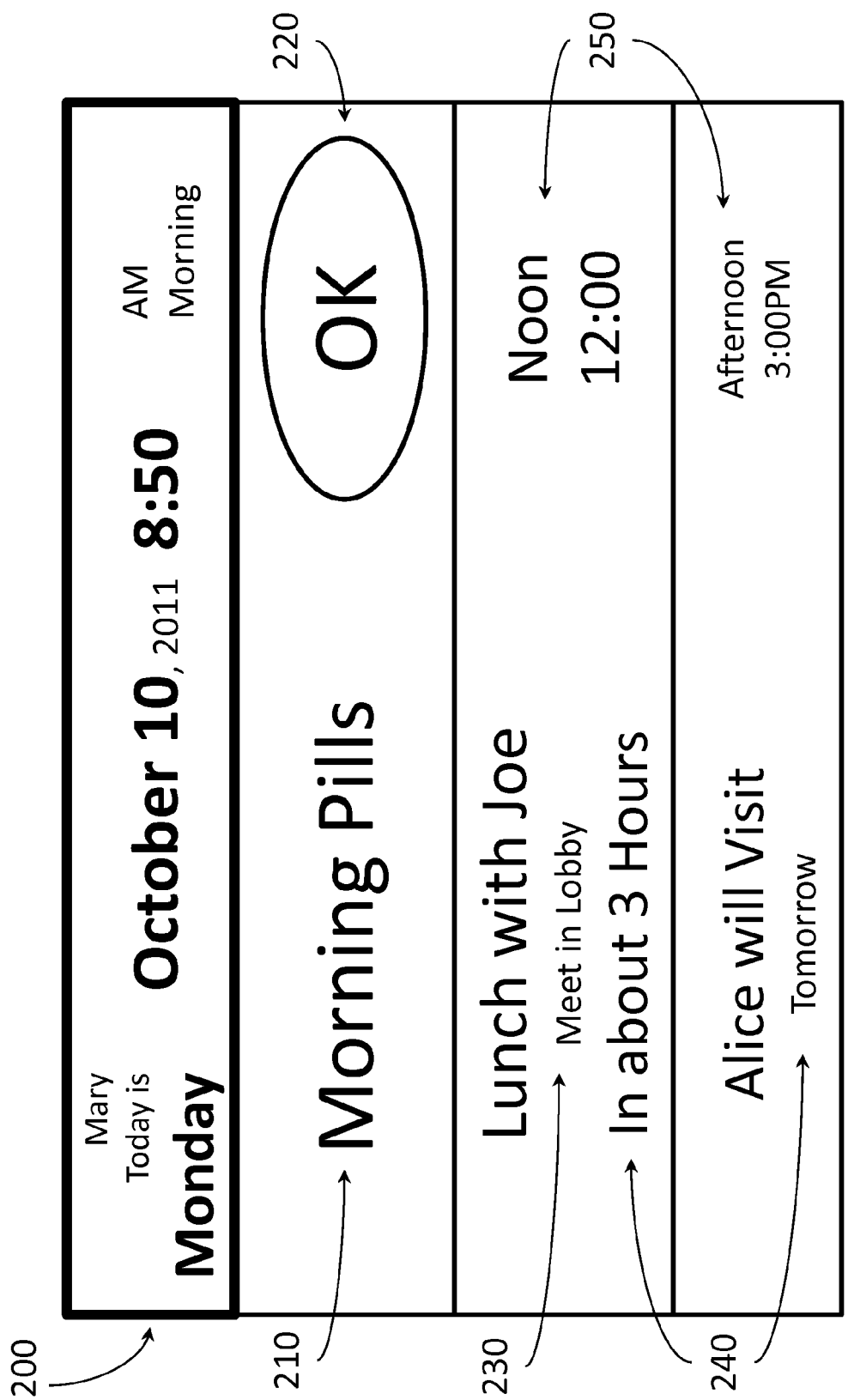
FIG. 2 shows an example messaging seen on a display device.

FIG. 2 illustrates a typical type set of messages that might be seen on a display. Because complex messages and even graphics can lead to confusion if a person has Alzheimer's, messaging must be kept simple, direct, and appropriate to the situation.

The top of the display 200 simply shows the current date and time. The part of the day, such as "Morning" or "Evening" is also shown. Time and date are automatically obtained from the network. Since the display can be in one time zone while a user is in another time zone, the display's time zone is determined by a selection 1710 made by the display's master user.

In the sample display, event or reminder "titles" 210 are shown on the left because the illustration assumes people tend to read from left to right. Of course, different cultures can work differently, and so adjustments to how the display is arranged can be adapted to different countries.

Message titles are kept deliberately short by limiting their length in the input menu 1100.

The size and font color used to display the message title (and other parts of the messaging) change according to how close they are to the event in question. The closer they are to the event's start (and end, if the event is of any length), the larger the font and more urgent the color.

Since message titles might be too short from some occasions, a second line 210 is allowed for putting additional messages or instructions. This second line is optional and can be made to not appear until the time gets closer to the event. This delayed showing of the second line follows the assumption that showing too much information too early would only confuse the reader.

Additional messaging 240, 250 is added to reminders to give clues on when an event is to take place. The wording of the supplemental timing messages is designed in a simple conversational style. It would be too confusing to the reader to say that an event is supposed to start at "11:30 AM, Apr. 10, 2011" if something like "In about 2 Hours" can communicate the same thing. The algorithms for how such timing messaging works can be fairly involved and must be tailored to the cultural and language norms of the viewer. As always, messaging must be kept to a minimum; but, it can also be a problem if too little information is given.

Figure 22:
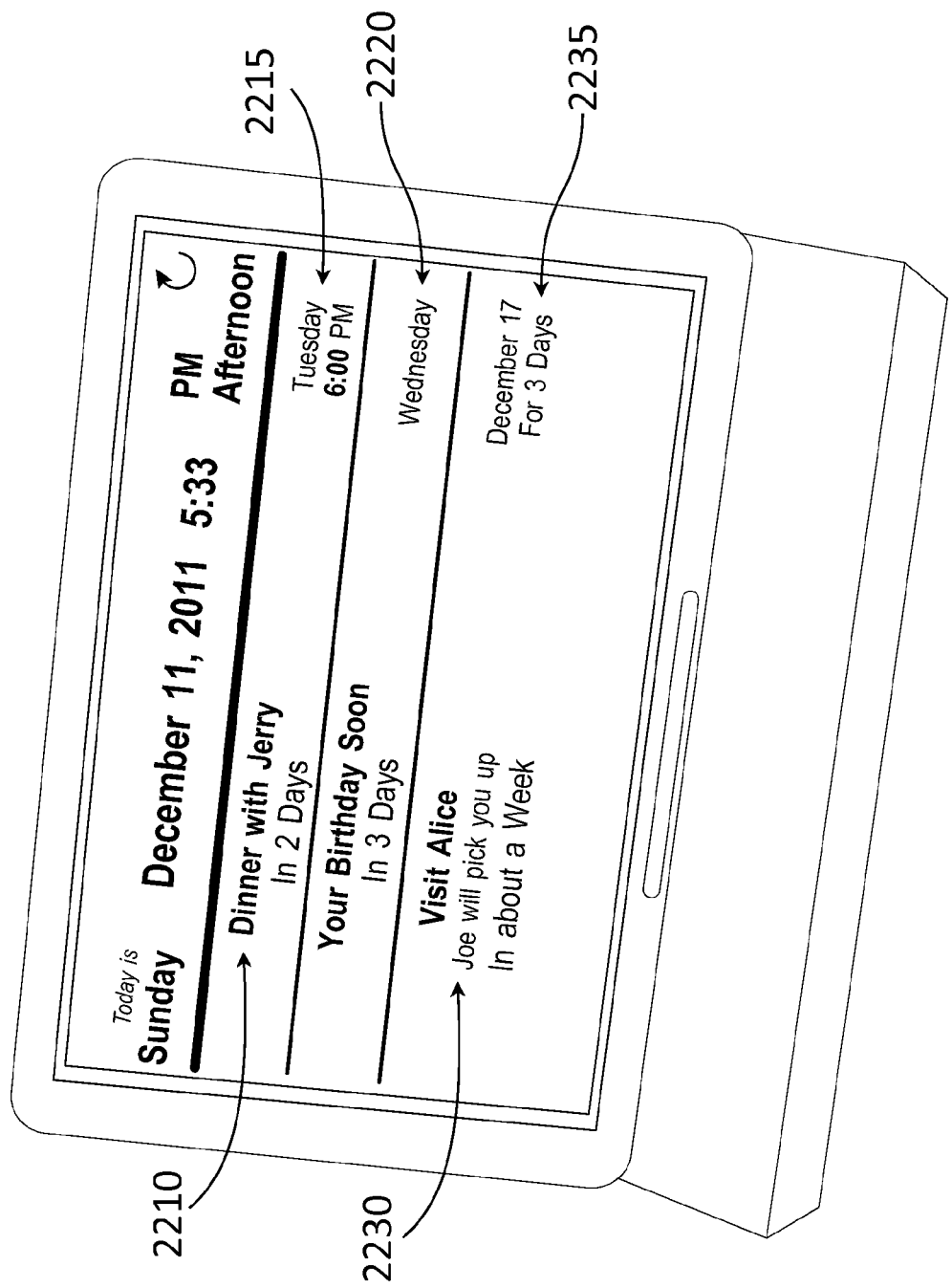
FIG. 22 depicts an example display device showing a few example reminder messages.

FIG. 22 shows more sample messaging on a working display.

The sample message "Morning Pills" is asking for a response—in this case the pressing of the "OK button" 220. Instructions on how to respond can be given verbally or by other means. In this illustration, the OK button is simply a graphic on the display, and the system senses the pressing of this button by using a touch-sensitive display 1015 system. The status of the response can be monitored, as will be explained later.

FIG. 3 shows a similar sample display to FIG. 1, but with one difference—the OK button has been replaced with a checked-box icon 320. This icon, or a similar type of indicator, tells the viewer that the message was acted on. Sometimes people will forget that they already acted on something that they regularly do, such as taking pills. The checked box icon serves as another form of reminder.

Figure 4:
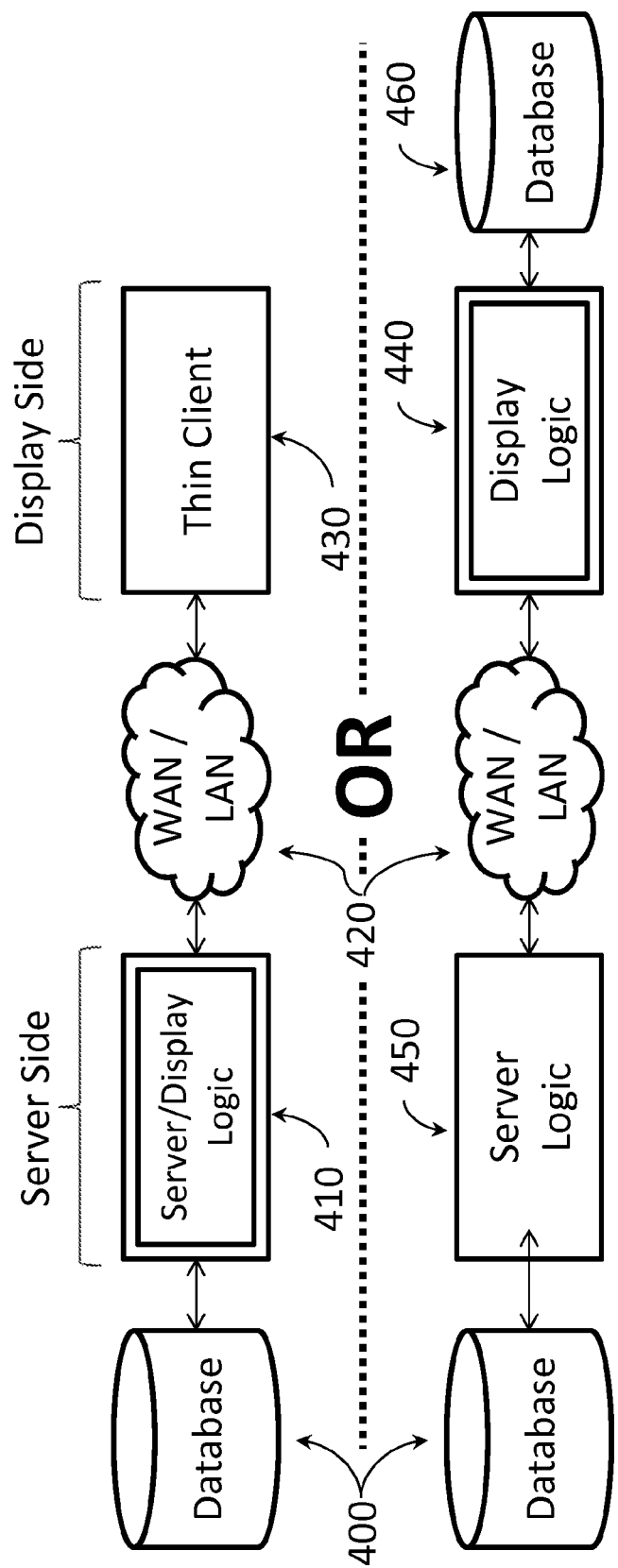
FIG. 4 shows examples of alternative approaches for where to place system logic within the overall system.

FIG. 4 shows a couple of ways to distribute the system's logic.

The top version places almost all logic in the server side 400, 410 and the display 430 is not much more than a thin client, such as a browser connected to the Internet 420. Such an arrangement means that off-the-shelf products, such as modern tablet computers, can be used for the display.

In this arrangement, the tablet computer is basically used as a browser display. HTML and PHP commands in various web pages determine what to display and when to display it.

Refreshing of the display just after the top of each minute, or at other selected times, is programmed into the webpage by reading the network time and calculating the time for the next auto-redirect command (header('Location: page_url.php')). Upon each refresh the display can update the displayed time of day, retrieve new messages, and update the wording and fonts of currently active reminder messages. Audio can be played, if required, via commands found in HTML5, or alternatives.

The bottom version places some of the messaging logic into the client side 440. Information on future events can be stored locally in the display's local database 460. Algorithms that have been placed into the display's system can then determine what to display at any given time without having to communicate with the server's system. The display will still need to periodically communicate with the server to get message updates, but such communication can be less frequent. Much of the system's logic, particularly for Master, Normal, and Group interfacing, account management and general system management, etc., still resides in the server 450.

Implementation can be done a number of ways. In one version, software code could effectively be downloaded into the display's browser using a language such as AJAX.

In another version, the display could contain a software application that stays resident in nonvolatile memory, if present. This software can be made to automatically execute when the display is first turned on. This means that power and communication interruptions can be automatically addressed.

Figure 5:
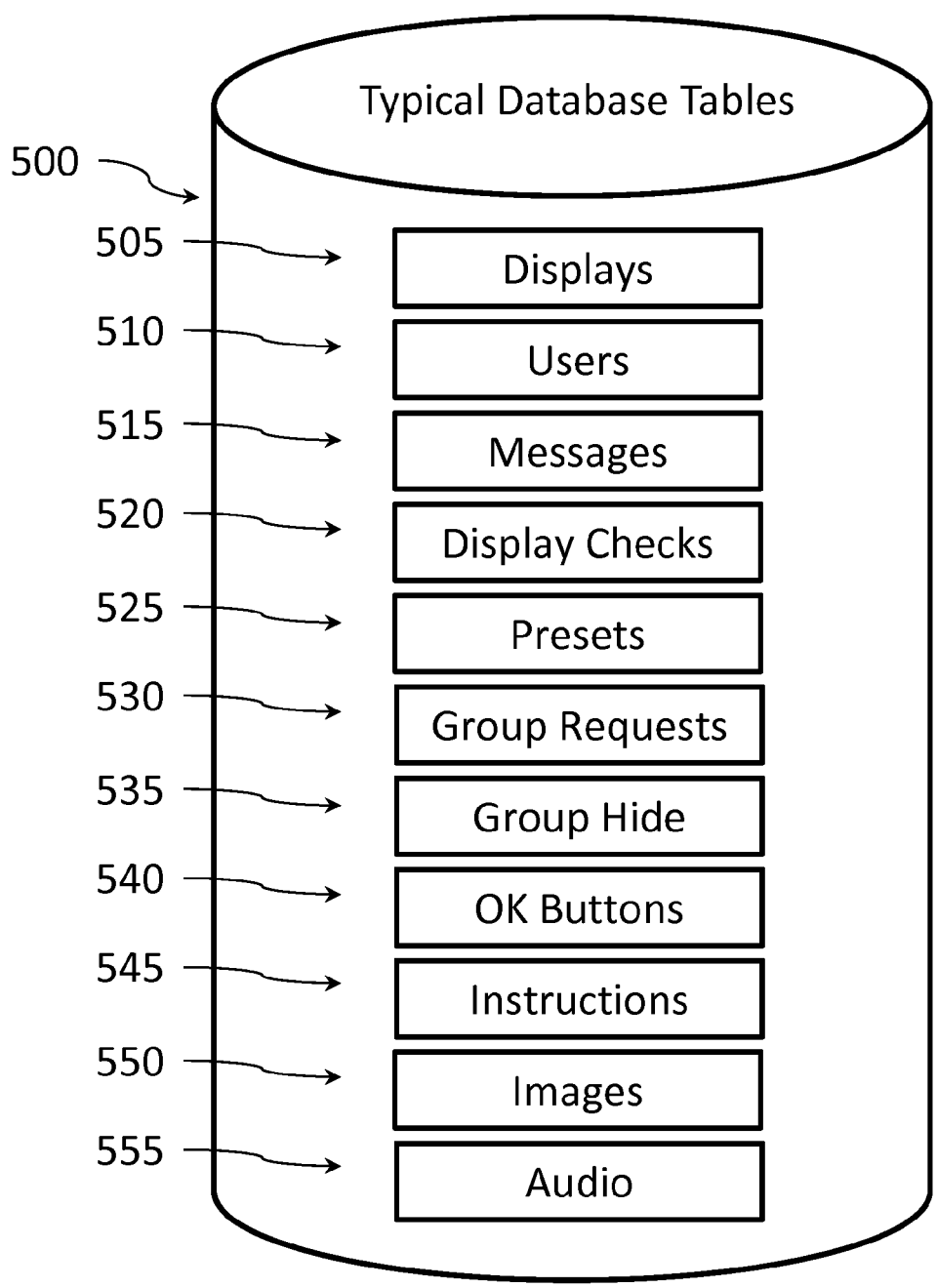
FIG. 5 illustrates exemplary database elements used by the system.

FIG. 5 shows categories of typical database 500 tables used in the system. During operation the algorithms stored in the server access the following database tables to determine how to handle each display, user and situation.

A table for Displays 505 contains information about each individual display, such as the names associated with the display and time zone. The table for Users 510 contains information on each user, including names, contact information, passwords, and type of user account. Users found in this table are associated with a display or set of displays (if this is a group user). The Messages table 515 holds all of the messages, including information on how and when each individual message should be displayed, who created the message, and the type of message. These three tables comprise the core of the database used by the system.

In addition to the core tables, there are a number of important supplemental tables. The Display Checks table 520 is used to store the health of each display. The Presets table stores predefined messages that can be used to save some typing. These preset messages contain most of the same information as regular messages stored in the Messages table. The Group Requests table is used to store requests that a Group User has made to Master Users to join a group. The Group Hide table is used to store information that determines if a particular Group message should be displayed on a particular display, or not. The OK Buttons table stores the status of responses for each message that requires such a response. The Instructions table is used to store localized (different languages) instructions and wording for the user interface. The Images table is used to store images that can be associated with particular messages. The Audio table is used to store audio files in appropriate formats that can be associated with particular messages or situations.

Figure 6:
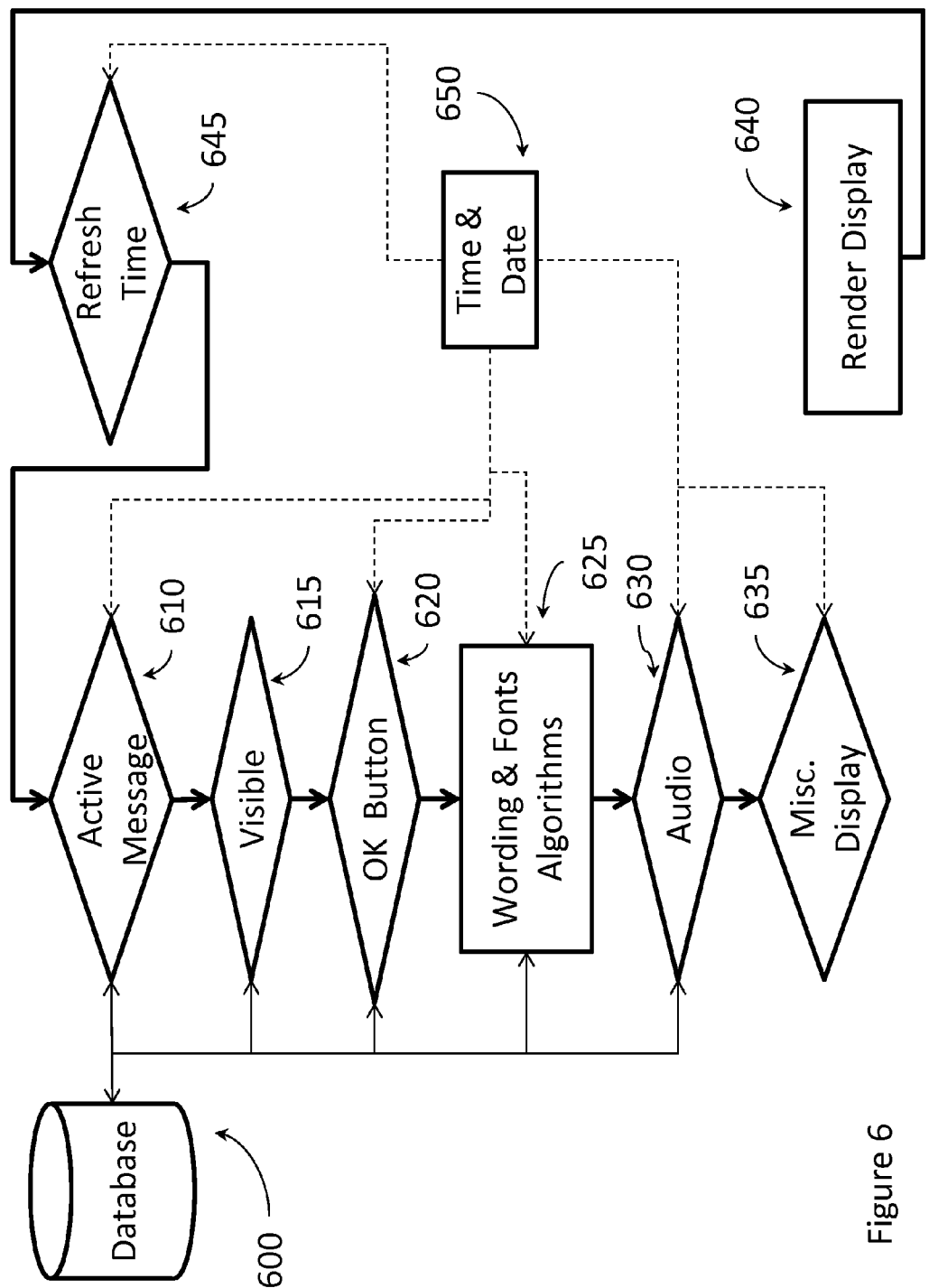
FIG. 6 provides an example of a simplified flow of logic for the display device.

FIG. 6 begins to show how the algorithms and database tables work together to manage all of the displays.

At periodic times the database 600 is looked at to see which messages are currently active 610. A message is active if the entry in the Messages table indicates that a message should be displayed based on the current time zone, date and time 650.

Next, if a particular message comes from a Group User, the Group Hide table is accessed 615 to determine if this message should be displayed on this particular display.

Next, the OK Button table is accessed 620 to determine if a response is required at this particular time or not. A message can be displayed without requiring a response until a predetermined time before the event is to start. Thus, for example, a viewer can see that an event is about to come up, but a response from the viewer is not requested until the event is just about to happen.

Next, based on parameters stored in the Messages and other tables, the exact wording and choice of fonts is compiled 625. How messaging is tailored to meet each situation is perhaps just as much an art as a science, but the important element of this disclosure is that such tailoring is integral to the system.

Next, if there is any audio associated with the message or situation, the Audio table is accessed and compiled 630 into the message as appropriate. As with the wording and fonts chosen earlier in the previous step, audio can be tailored, too.

Similarly, if there are any graphics or images associated with the message, these are also integrated in 635. Again, tailoring to fit the situation can be done.

Finally, the complete compiled message is rendered on the display 640. This includes any text, audio and/or images that were determined to be part of the message in earlier steps. The display and message is then refreshed as necessary based on the refresh timer.

Figure 7:
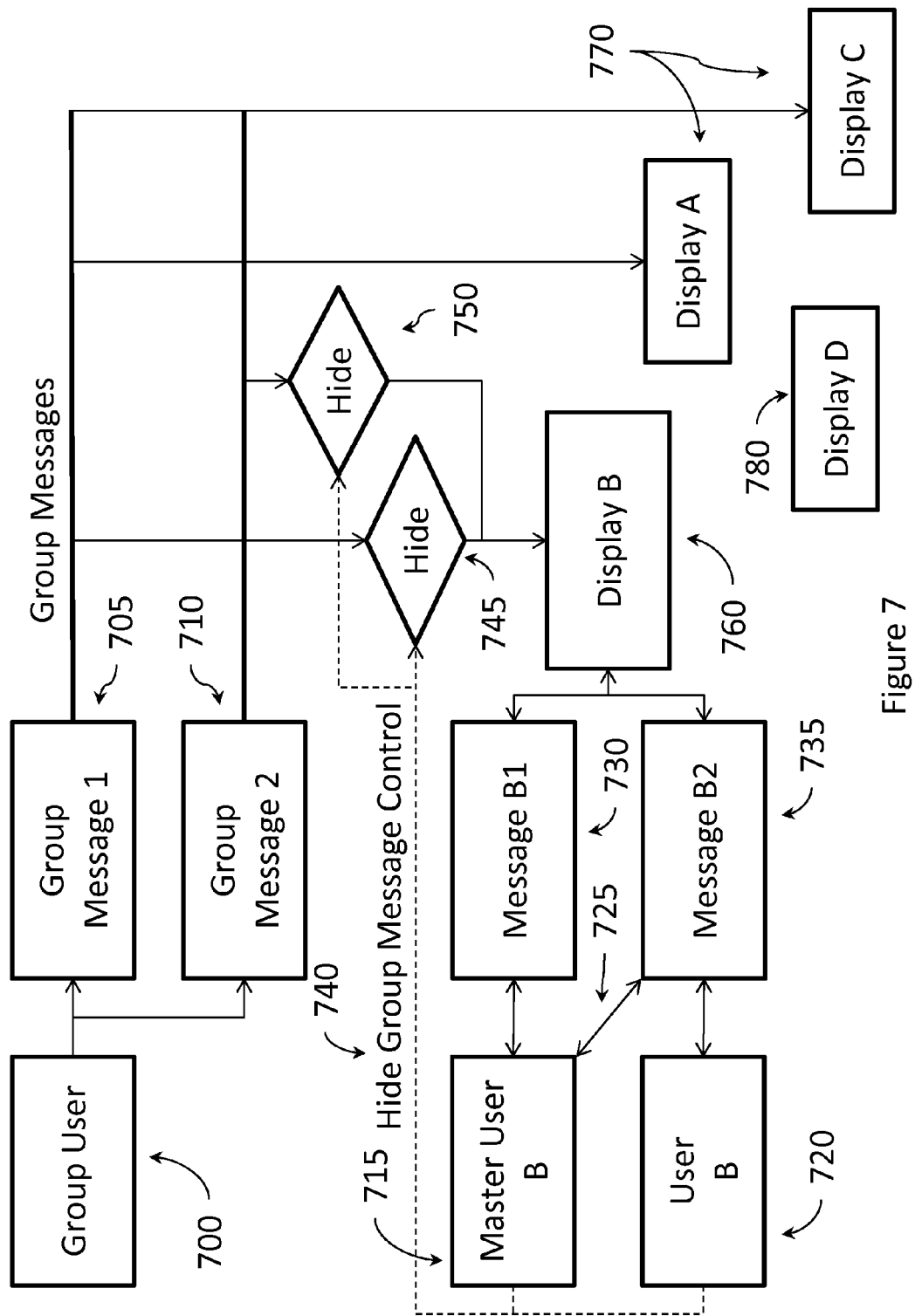
FIG. 7 shows the relationship of group messages and different types of users for a particular display device.

FIG. 7 shows a part of the relationship between a Group User 700, Master User B 715 and regular User B 720 when placing messages on a particular display.

The simplest situation is when a Master User wishes to place a Message B1 730 onto the Display B 760. Since Display B is managed by this user, the message is allowed. Other displays in the network, such as Display A, Display C 770 and Display D 780, ignore Message B1. Similarly, User B can place a Message B2 735 onto the same Display B because this user has been authorized by Master User B to do so.

Master User B also has the ability to edit or delete Message B2 that was created by regular User B. But, while regular User B can also edit Message B2, this user cannot edit Message B1 created by Master User B.

Both Master User B and regular User B can see all of the messages that are directed to Display B, whether or not they are currently showing on this display.

The Group User in this diagram is shown as creating two Group Messages 705, 710. These group messages potentially go to all displays 760, 770 that belong to this group, but not displays 780 that are not part of this group, even if such displays are on the same network.

When a Group Message is directed at any display, the Master and regular Users associated with that display also see this message. If either the Master or regular User decides that a Group Message conflicts with a planned event, the user has the ability to hide this Group Message. Each individual Group Message can be allowed to show or be hidden, so Group Message 1 705 can be hidden 745 independently from Group Message 2 710 being hidden 750. Decisions by this Master User B and regular User B do not affect what is shown or not on other Displays 770, 780.

Figure 8:
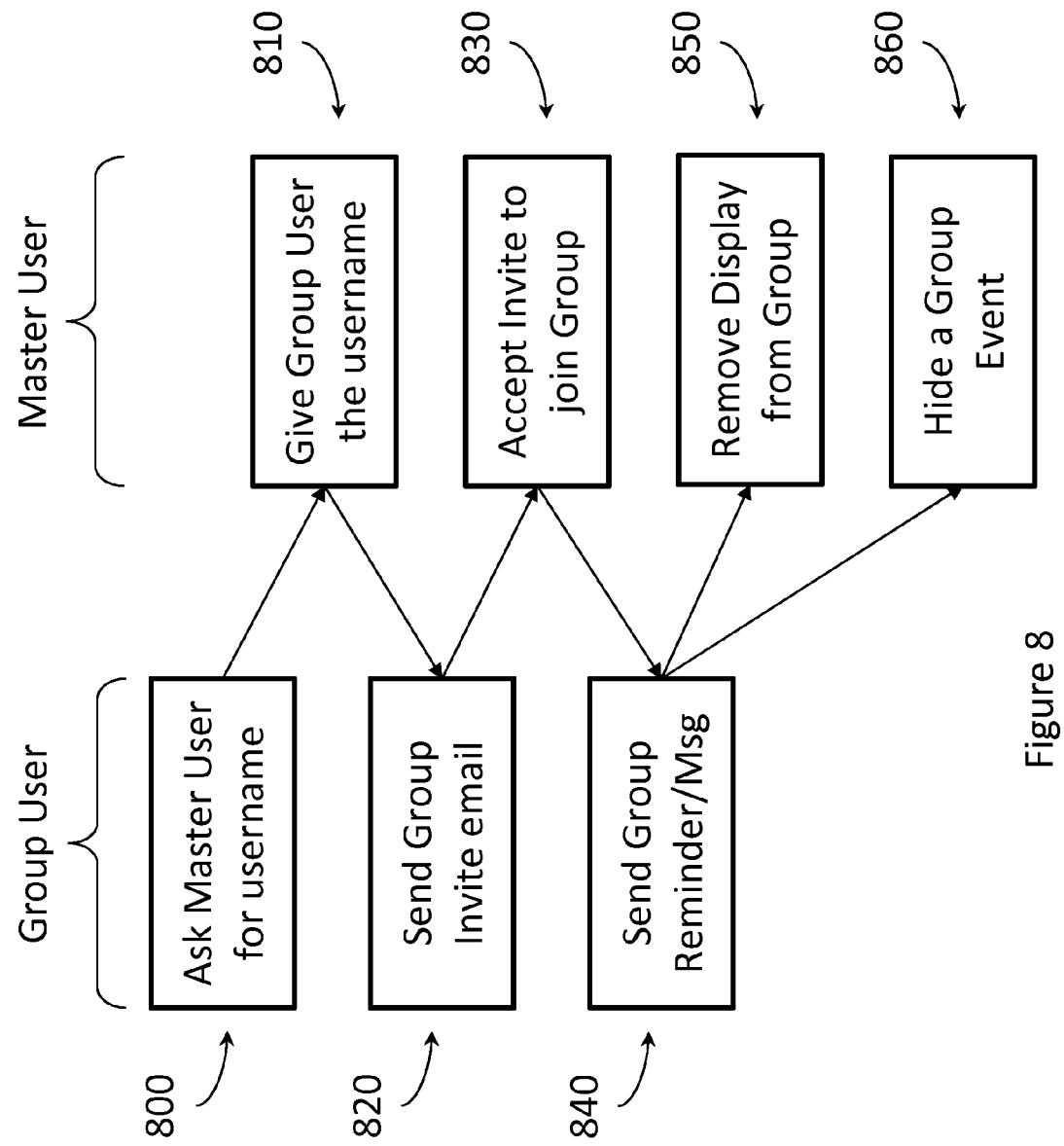
FIG. 8 shows an example process for setting up a relationship between group and master users for a display device.

FIG. 8 shows the flow of activities that determine if a particular display is part of a particular group. Control of the display belongs to that display's Master User, so the Group User must first ask for the Master User's username 800. If the Master User agrees 810, the Group User can then send that Master User an invitation via email to join the group 820. This email contains a special link with an encrypted key that, when clicked, takes the Master User to a web page that displays the group the display just joined 830. From this point the Group User's Group Messages will be seen on the display in question 840, unless the Master User decides to remove this display from the group 850 or hide that particular Group Message 860. Normal Users can also hide individual Group Messages (similar to step 860), but cannot remove the display from the Group.

Figure 9:
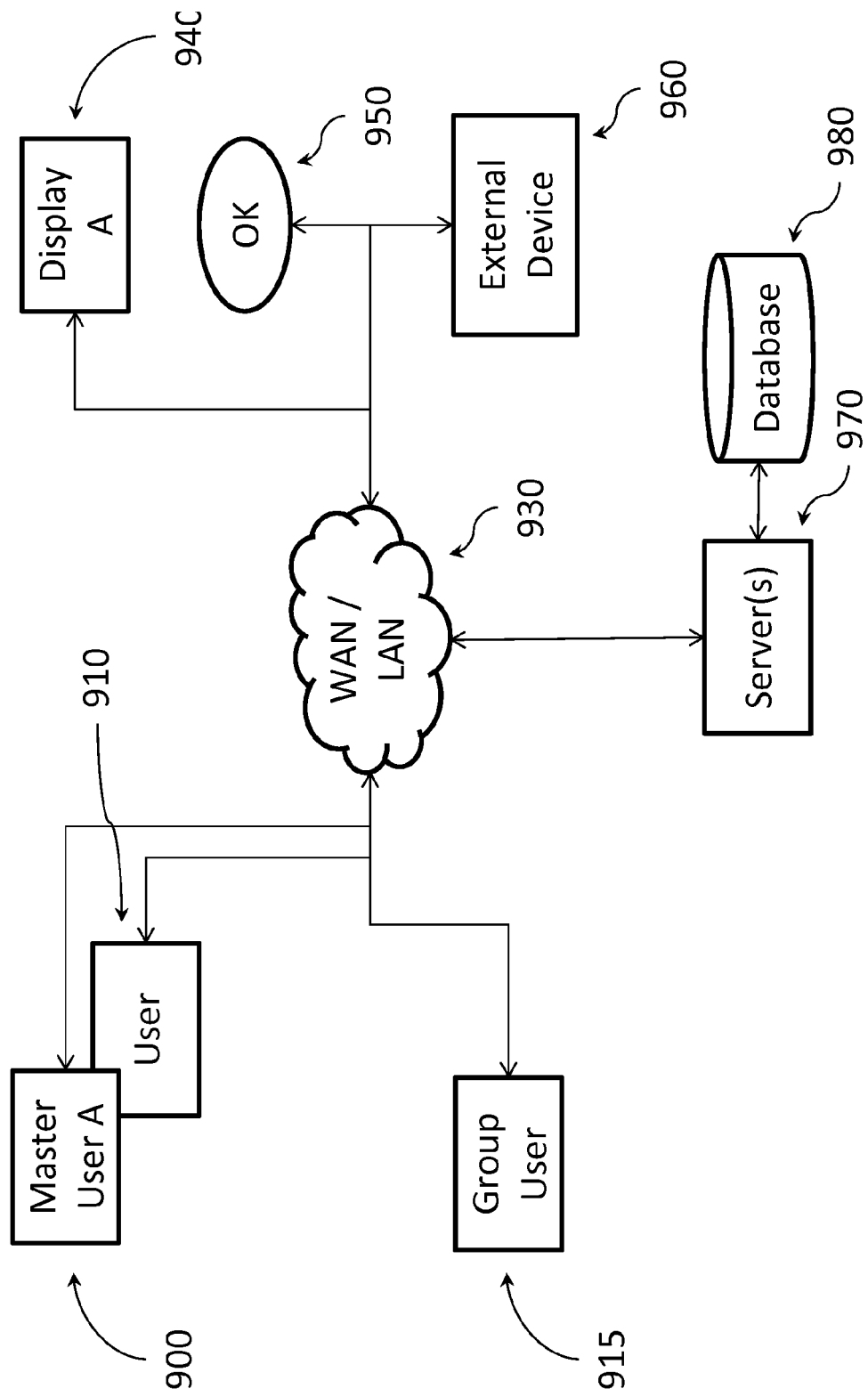
FIG. 9 illustrates a subset of a system for illustrating reminder acknowledgement.

FIG. 9 shows a variation of FIG. 1, and is used to illustrate how the OK button or acknowledgement system works. First, a reminder message is created by the Master 900, regular 910 or Group User 915 that specifies the need for an acknowledgement by the display's viewer. The message is saved in the database 980 and served up 970 to the display 940 at the appropriate time. Then, at the specified time, the OK button is displayed 950, along with any other verbal or visual prompts. Alternatively, an external device 960 can be activated to ask for some type of action. The requested acknowledgement is then made by the viewer and logged into the database 980. The various users can then see via a web page if the acknowledgement was made. Alternatively, the server can send a short message (SMS), email or even make a phone call.

Figure 10:
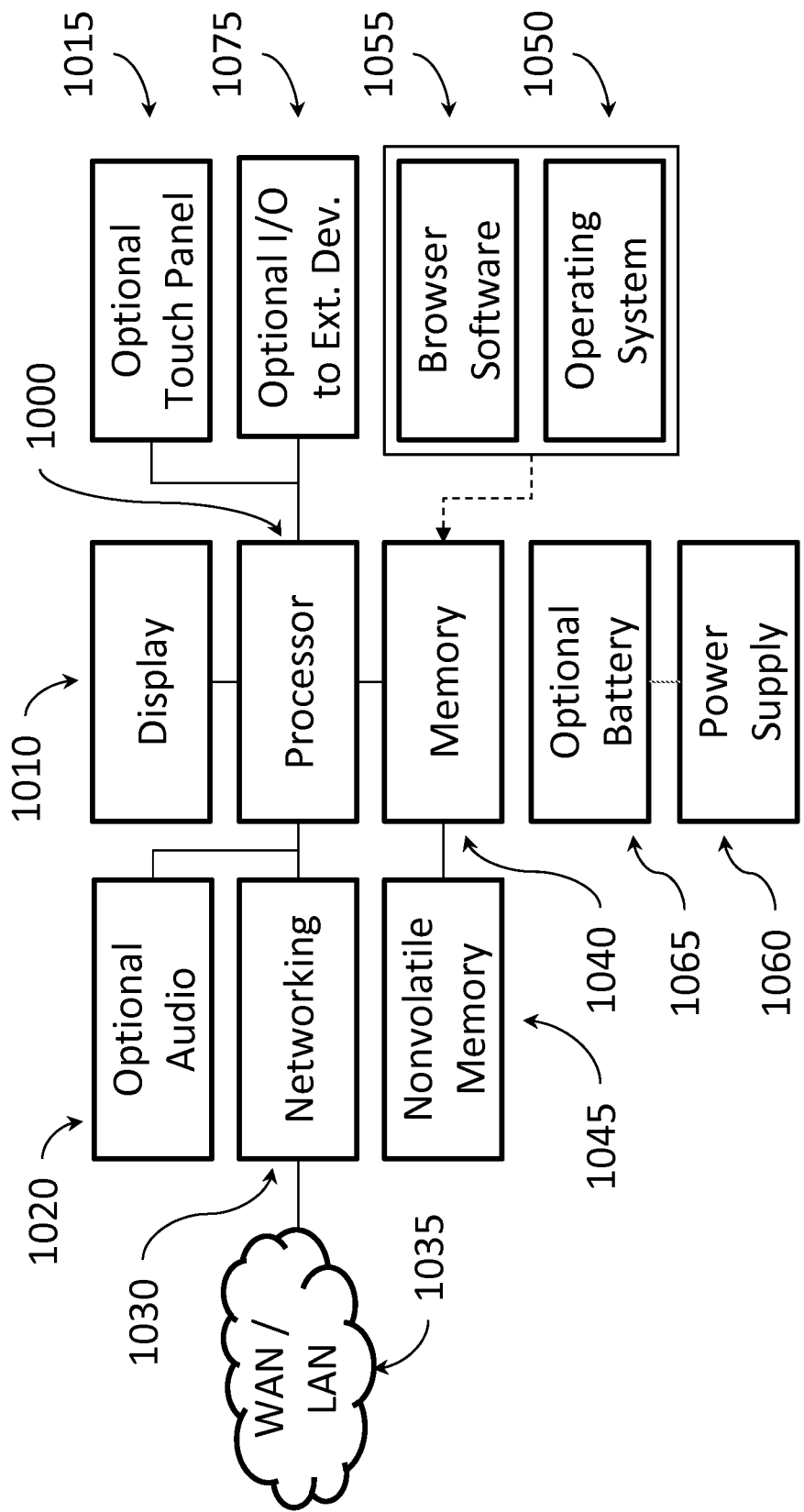
FIG. 10 shows an exemplary hardware block diagram for a display device.

FIG. 10 shows a typical hardware block diagram of a display. The display consists of a typical set of elements, including a processor(s) 1000, memory for instruction operation and variables 1040, nonvolatile memory 1045 for BIOS, operating system 1050 and applications 1055, power supply 1060 and optional battery 1065, display 1010 and optional touch panel system 1015, networking (wired and/or wireless) 1030 for connecting to the WAN/LAN 1035.

This display can be a stand-alone product or be part of another product. For example, this display can be integrated into a television. If so, the touch panel user interface might be replaced with a remote control arrangement. Since most all of the other elements are already part of today's televisions, these elements can be shared and leveraged.

Figure 11:
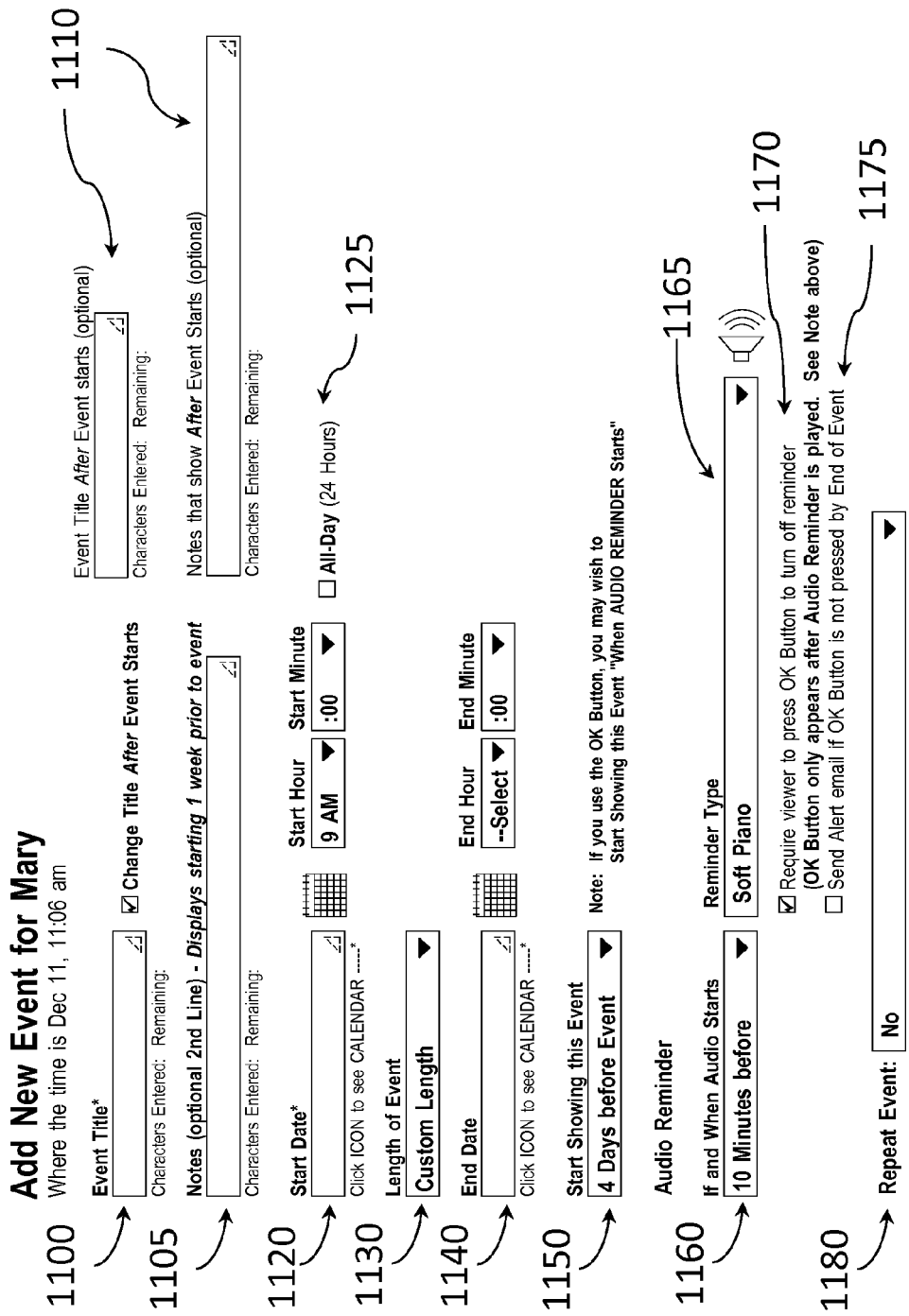
FIG. 11 illustrates an example user interface for creating and/or editing reminder messages.

FIG. 11 shows an example user interface screenshot for entering or editing a reminder message. This can be part of a webpage or be part of an application.

It begins with a place for entering the message title or headline 1100. There is also a place to enter a second line of description 1105. While there can be even more lines, this illustration limits descriptions to just these two parts to keep the message to the viewer simple.

Sometimes it helps to change the message once the event starts. For example, a message can read "Your Birthday Soon" on days leading up to the birthday, but read "Happy Birthday" on the day of the birthday. To accommodate this option, a second set of message titles and notes are allowed for 1110.

Each reminder message is then given a start date and time 1120. Some types of events, such as holidays and birthdays, are really about the day itself, so events can be designated as being "All-Day" 1125.

If the event is not an All-Day event, the next thing to specify is how long the event lasts 1130. If the event lasts less than a day, the length of the event can be specified in minutes, hours, etc. If the event takes place over multiple days, the end of the event can be defined by specifying a specific date and time 1140.

Next, one can specify when to start showing the event on the display 1150. The timing of when to start showing the event is highly dependent on the type of event and preferences of the users and viewers, and is not tied to the length of the event.

Optionally, audio reminders can be played to draw attention to an event. One can specify when to start playing such audio messaging 1160 independently from when the event starts to show, except that audio messaging should not start until the message shows visually. The type of audio messaging can be chosen separately 1165.

If an acknowledgement of the reminder message is required, there is a checkbox that the user can check 1170. Further, if the user wishes to be alerted if acknowledgement is not given after a specified period of time (by the end of the event), another checkbox 1175 is provided for doing so.

If the event repeats in some predictable way, the system lets the user specify how this event should repeat 1180. A number of repeat options, from daily to yearly, and several options in between, can be provided. Unlike calendar systems used in PC, PDA and phone systems, only one occurrence of a repeating event is shown at a time to avoid confusion by the display's viewer.

Figure 12:
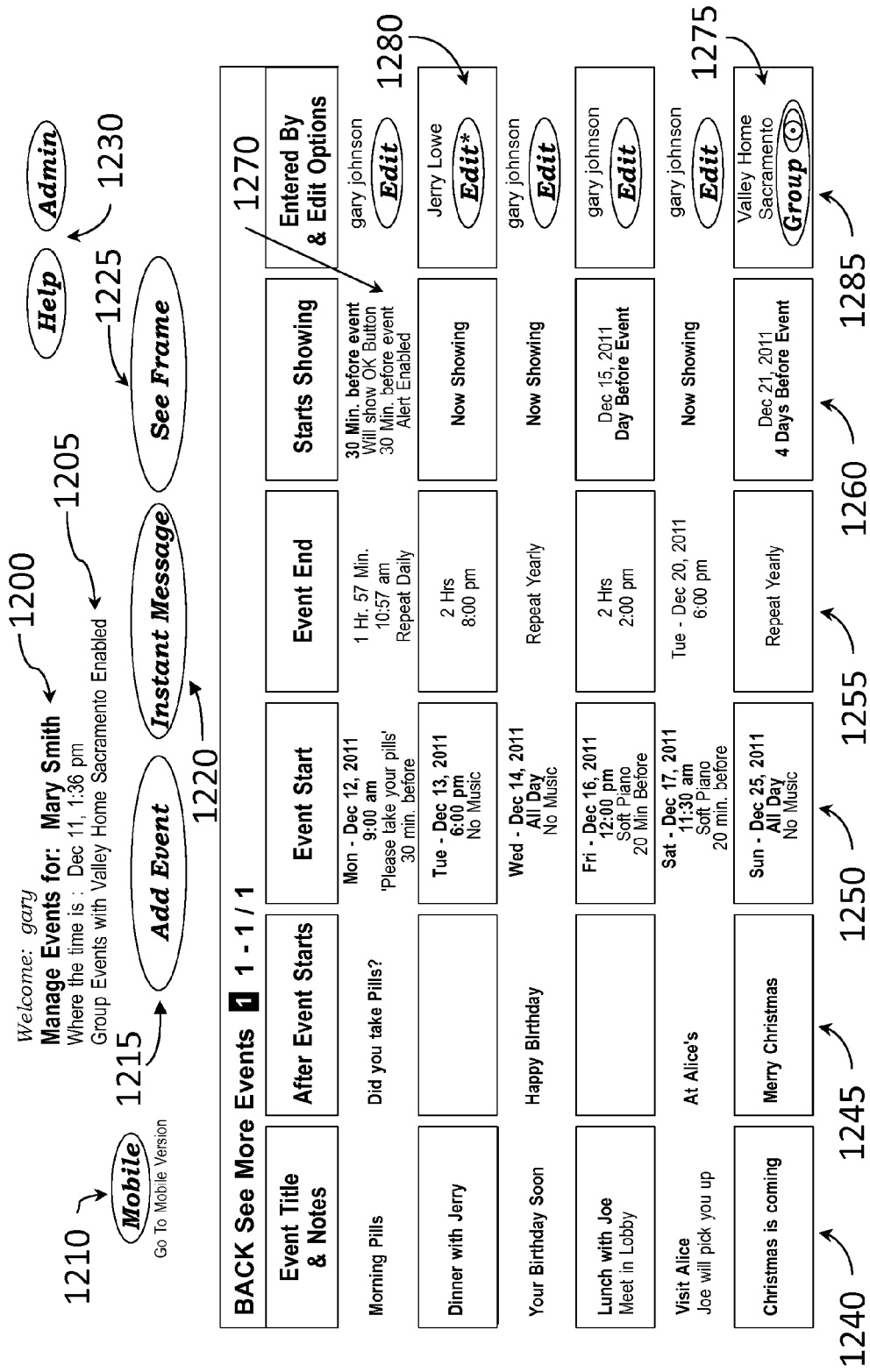
FIG. 12 illustrates an example user interface as seen by a master user for reviewing all active reminders and messages for a particular display device.

FIG. 12 shows a typical user interface that Master Users see for reviewing and managing all of the messages scheduled to show on the display. This can be found on a webpage or be part of an application.

The interface shows information about which display it is showing 1200, plus other supplemental information such as the time where the display sits, and if this display is enabled to accept Group Messages 1205.

There is a button for showing the information in a format that is friendlier for mobile devices 1210 (automatic switching to this mode is also possible). There are buttons for adding a new reminder message 1215 or instant message 1220. There is a button to see what the display itself looks like at the moment 1225. There are other buttons for displaying help and infrequently used administrative functions 1230.

The main table shows a summary of all of the active events currently lined up for this display. Table columns show titles and notes (1240, 1245), information on when events start and what the display should do at various times 1250, information on when events end and if or how they should repeat 1255, information on when events should start to show, or if they are currently showing on the display 1260. There is also information regarding whether acknowledgements will be requested, or whether an acknowledgement has been given or not, and if an alert should be issued if an acknowledgement is missed 1270. A final column shows who created the message 1275, and shows an edit button if the message is one that this user can edit 1280. Since FIG. 12 is for a Master User, this user has edit privileges for any message created by any other Master or regular User. The edit button can be made to look slightly different if the particular message was made by someone else 1280.

Not illustrated is a flag that appears if two or more events overlap or conflict. Since different users can be placing event reminders onto the same display, one user could accidently create an event that conflicts with another, so it is important to give some indication of such a conflict.

For Group messages, instead of an edit button, there is a button that is used to hide or show that Group message. In this case, the button shows an open eye 1285 if the message is visible, but a closed eye if it is not. Specific implementations of this feature can be different according to user interface preferences.

FIG. 13 shows a similar illustration for managing reminder messages, only this one shows what it might look like for Normal Users. Since Normal Users can only edit messages that they entered themselves, the edit button only shows on a subset of the listed messages 1300, and not for messages that others have created 1310. Since Normal Users can hide and show Group Messages, they still see the button for doing so 1320.

Figure 14:
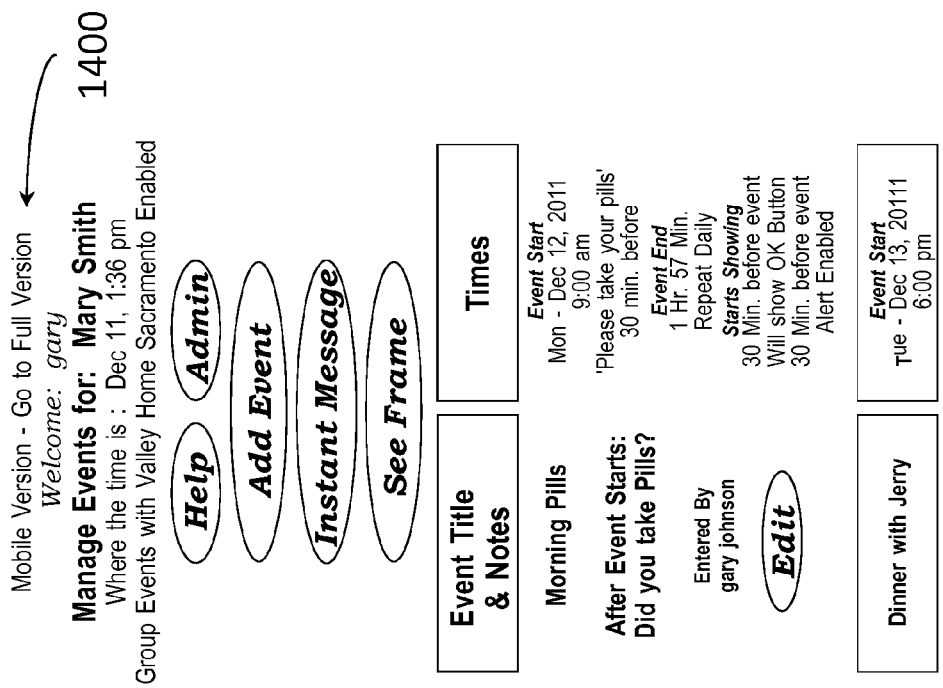
FIG. 14 illustrates an example of a similar user interface formatted for smart phones and other mobile devices.

FIG. 14 shows what these interfaces might look like for a mobile device. Only part of the overall interface is shown—the rest can be seen by scrolling or paging. There is also a way to get to the "full" interface 1400.

Figure 15:
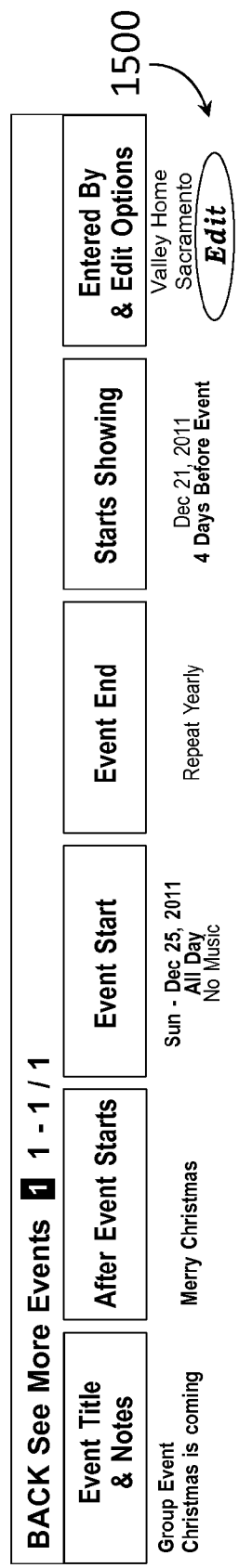
FIG. 15 illustrates an example user interface as seen by a group user for viewing group reminders and messages.

FIG. 15 shows what the interface might look like for a Group User. Since the example being used only had one Group Message in it, only one message 1500 is shown on this table. Unlike Master and Normal Users, a Group User can edit a Group Message, so we also see an edit button.

Figure 16:
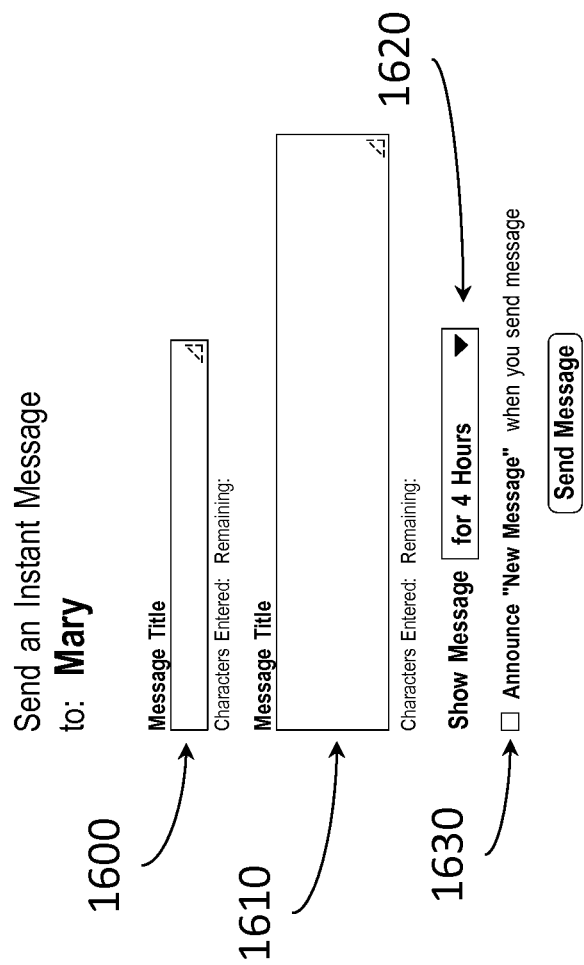
FIG. 16 illustrates an example user interface for creating or editing an instant message.

FIG. 16 shows a typical interface for sending an Instant Message to a display. A place for a message title 1600 and second line of details 1610 is given. A way to specify how long the message should be displayed is then provided 1620.

Unlike typical instant messages used on phones or PCs, the viewer of the type of display described in this disclosure is a more passive viewer. No action is required by the viewer to get the message onto the display, but at the same time, there is no guarantee that this person will ever notice the message. To draw attention to the message an audio notice can be specified 1630. Alternatively (not illustrated here), a message can be made to request an acknowledgement, similar to messages illustrated earlier.

Figure 17:
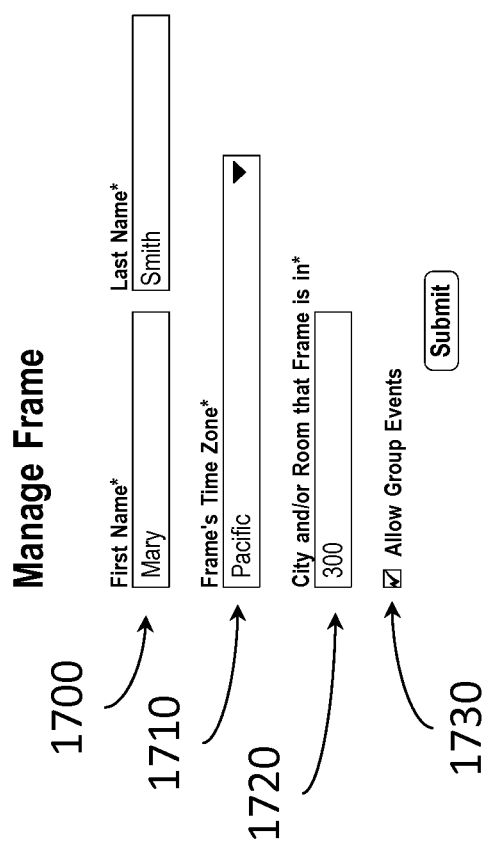
FIG. 17 illustrates an example user interface for managing parameters for a particular display device.

FIG. 17 shows a part of the system's administration functions—in this case the management of the display (or "Frame" as it is called in the illustration). Each display can be given a name 1700, which is generally the name of the person that will be viewing the display. Next, is a way to specify the display's Time Zone 1710. Alternatively, time zone information can be obtained via the network that the display is connected to.

Some form of location description, such as city or room number, can be specified next 1720. The combination of display names and location help to uniquely identify each display.

If it is OK for this display to accept Group Messages, a checkbox 1730 is provided for doing so. This checkbox is automatically checked when the Master User clicks on the email invitation 830, but can be subsequently unchecked or rechecked at any time.

FIG. 18 shows an interface for managing Preset reminders. Some Preset reminders are defined by the system and are shown here as coming from Admin 1820. Some presets might have been defined by a Master User, Normal User or Group User. If the user has edit privileges (which follow rules similar to regular reminder messages), an edit button will appear 1810.

Figure 19:
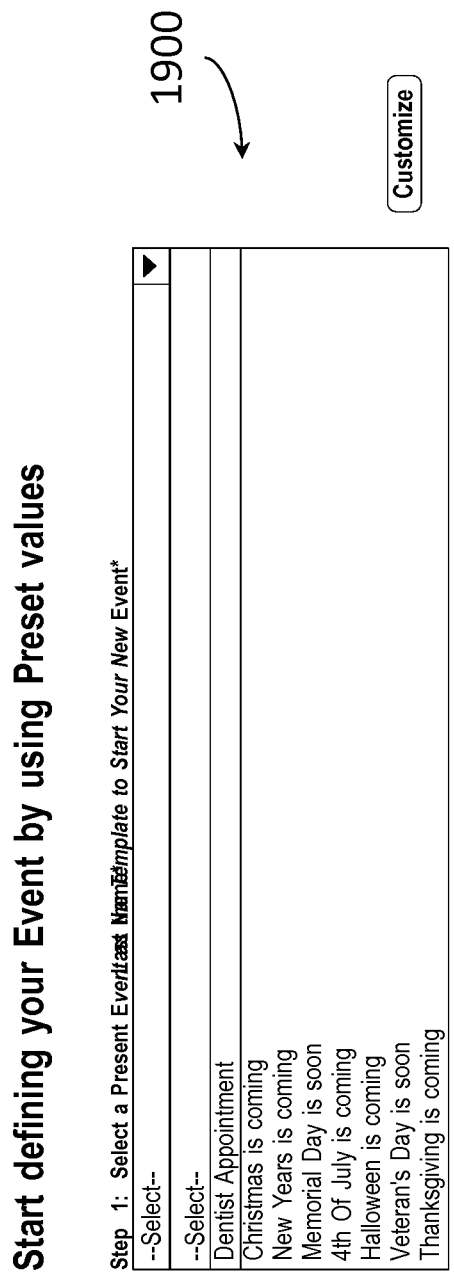
FIG. 19 illustrates an example user interface for selecting a preset reminder.

FIG. 19 shows a simple way for picking a Preset. Once Presets have been defined, they are available for picking 1900 when creating a new reminder message by clicking on a button for Presets (not illustrated, but it would be found on an interface similar to that shown in FIG. 11). Once a Preset is selected, it can be subsequently modified and customized. Thus, users are not locked into a particular set of parameters, dates, times, etc.

Figure 20:
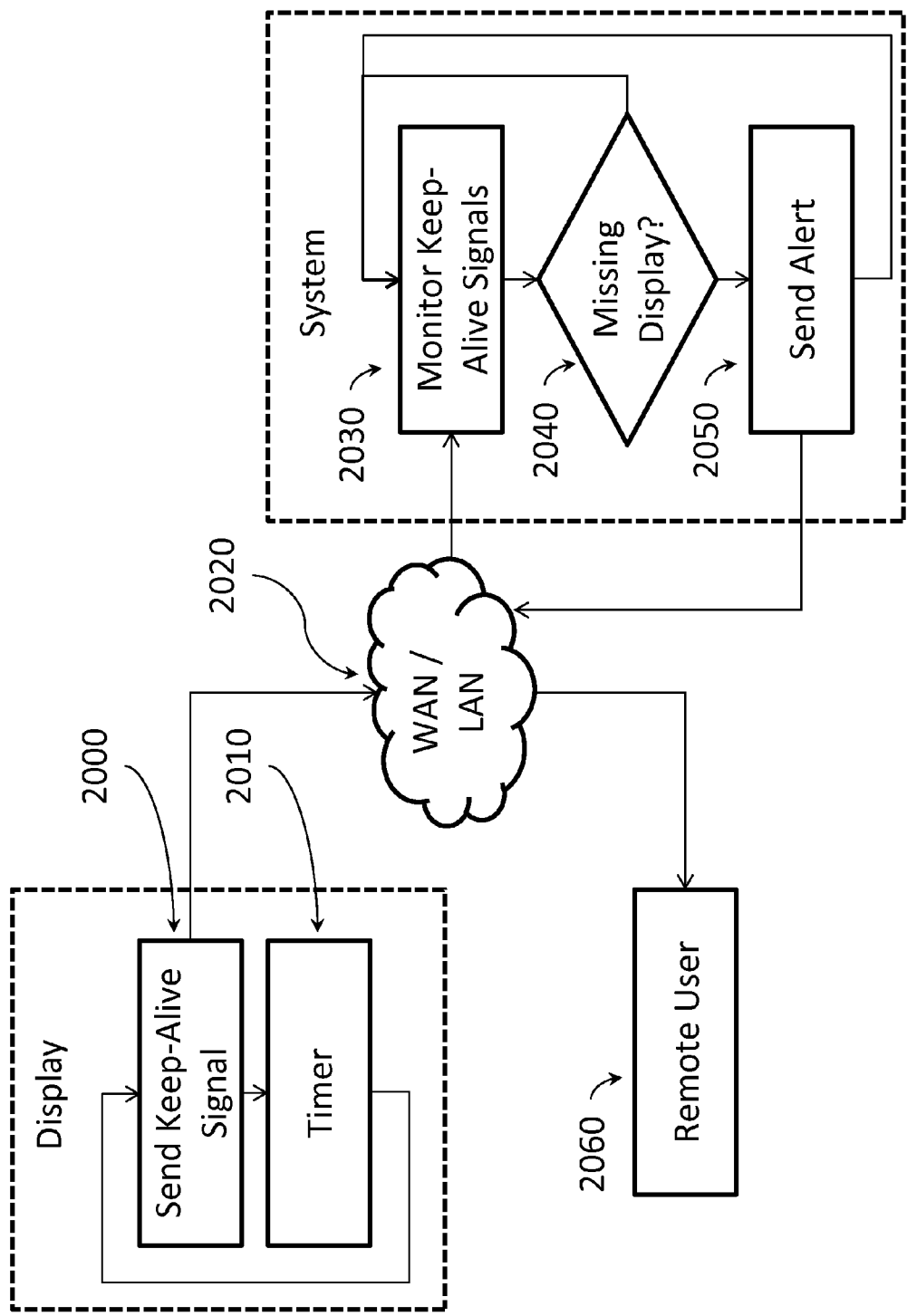
FIG. 20 is a diagram for showing how a display device's health can be monitored.

FIG. 20 shows a low-level operation designed to monitor the health of a given set of displays. Displays can be accidently turned off, lose power or communications, or have a hardware failure. Since the display is usually not near the people that manage it, there needs to be a way to get some indication about its health.

To do so starts with the display sending out a periodic "keep-alive" signal 2000 to the server via the network 2020. The frequency of this keep-alive signal can be preset 2010 and does not need to be too frequent, depending upon needs.

The server ("system" in this illustration) accepts the keep-alive signals from all of the displays that it is monitoring 2030. If one or more of the displays fails to send a keep-alive signal 2040, an alert can be sent 2050. Alternatively, a webpage can be updated to show the suspect display name and location.

Meantime, Users 2060 can view the status of the display and/or receive alerts even though they are nowhere near the display.

Figure 21:
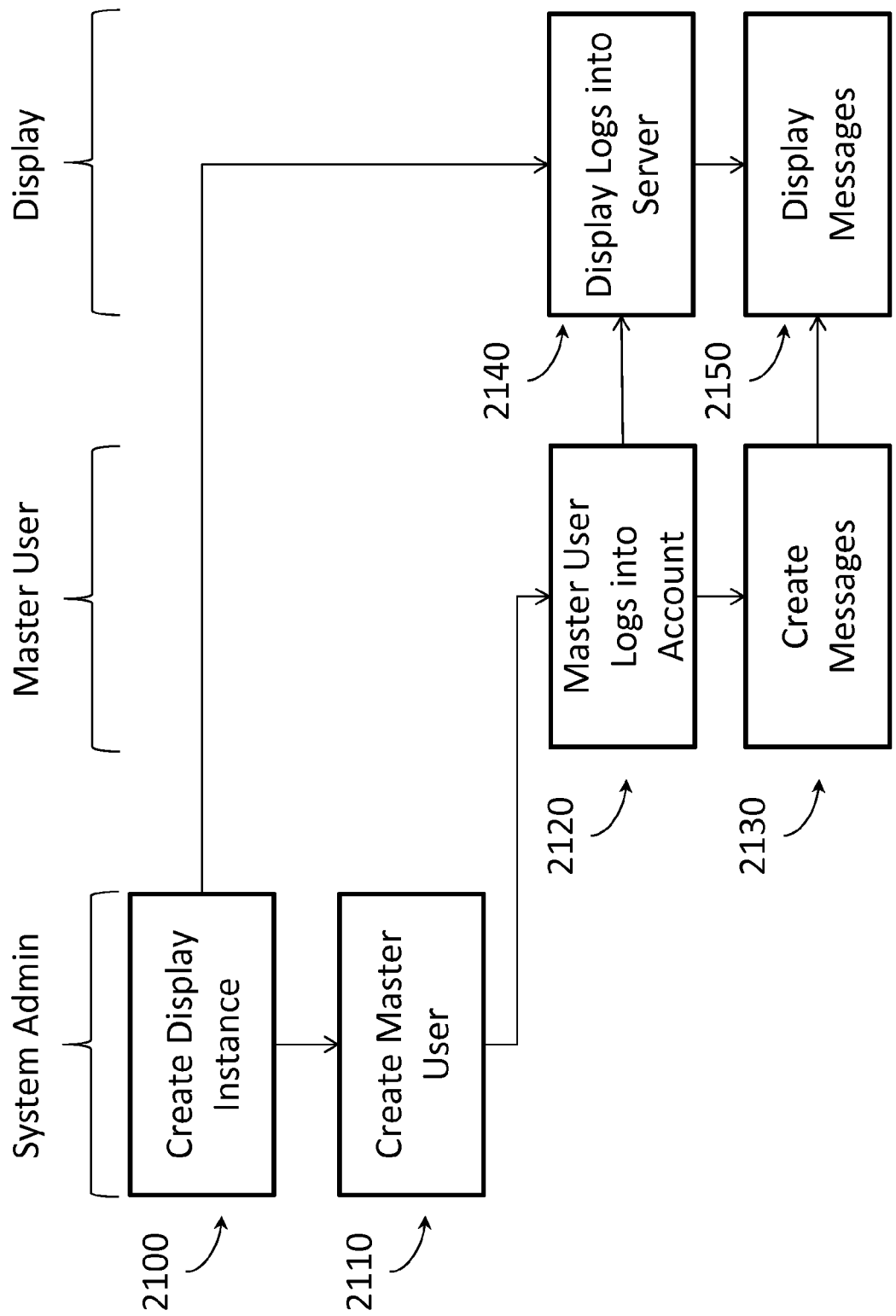
FIG. 21 depicts the display and master user setup.

FIG. 21 shows another low-level admin function, display, and Master User setup.

For each display a unique account needs to be created. This account can be created by a system administrator 2100. This administrator can be a service provider or someone at a factory. If the display is a unique device made specifically to work in this system, a unique account code, probably algorithmically generated, can be stored in the display's nonvolatile memory. If a service provider is creating the display's account, any number of means may be used to create unique codes. Once created, these unique account codes are also stored in the system database 160, 505.

Next, the system administrator creates a new Master User account. This account consists of a unique username and a pointer to a specific display. A password, advisably unique, is also generated. Again, if the display is made specifically with this system in mind, the Master User setup can be done in the display's factory. Alternatively, a service provider can create the Master User account details. Either way, once created, this information is also stored in the same database 160, 510.

Next, the new Master User is given the new username and password. This Master User then logs into the system 2120. Once logged in, this person can create new reminder messages 2130, create other users, etc., as described earlier.

Before or after this step the Master User installs the display where it is intended to be used (e.g., the person with Alzheimer's). Installation consists of logging the display into the system 2140. Logging into the system involves two steps. The first step is to establish a network connection. This connection can be accomplished in a number of ways depending upon the specific type of network connectivity used. Connectivity can be accomplished via various wired (e.g., LAN via a cable, modem via phone) or wireless (e.g., Wi-Fi, cellular, Bluetooth) means. For example, if there is an existing Internet service available via a Wi-Fi connection, the display would first need to establish a link to this Wi-Fi.

The second step for logging the display into the system is to make the system aware of the display's unique identification code established earlier 2100. This step can be done manually or automatically by the display.

If done manually, a screen on the display would request the display's account log-in information, such as a username and password. The user could use any of a variety of input devices (e.g., touchscreen, remote control or keyboard) to enter the required information.

If done automatically, the display would read its unique identification information from nonvolatile memory and pass this information to the system. Automatic logging-in of the display can be done once the display's nonvolatile memory is loaded with the required information, either by the factory or the Master User.

Passwords, in particular, would be encrypted before being passed to the server. Encryption is necessary to preserve privacy.

FIG. 22 shows a prototype display device. It is in a stand so that it can be placed on a tabletop. Alternatively, such a display can be built into a wall or be part of another device, such as a television.

Notice that similar to FIGS. 2 and 3, messaging is tailored to fit the current time relative to each event. For example, "Dinner with Jerry" is shown as "In 2 Days" 2210, which is a Tuesday at 6 PM 2215. The birthday is "In 3 Days", and since this is an All-Day event, no time of day is given—it just says it is on "Wednesday" 2220.

A "Visit Alice" event shows a bit more detail 2230. This happens to be a multi-day event, so we see that it starts "In about a Week" on "December 17" and lasts "For 3 Days" 2235.

Each of these messages will automatically change over time, depending upon how close to the event it is, and if the event has started, or just ended.

The illustrated sample display has a white background because the photo was taken during the day. To reduce the possibility of disturbing someone sleeping, during night hours the display's background becomes black and font colors are adjusted accordingly for readability. Timing for when the display goes into night mode can be arbitrary, set by Master User selected options, or automatically adjusted according to where in the world the display is located, as determined by the geo-location of the IP address detected by the display.

Figure 33:
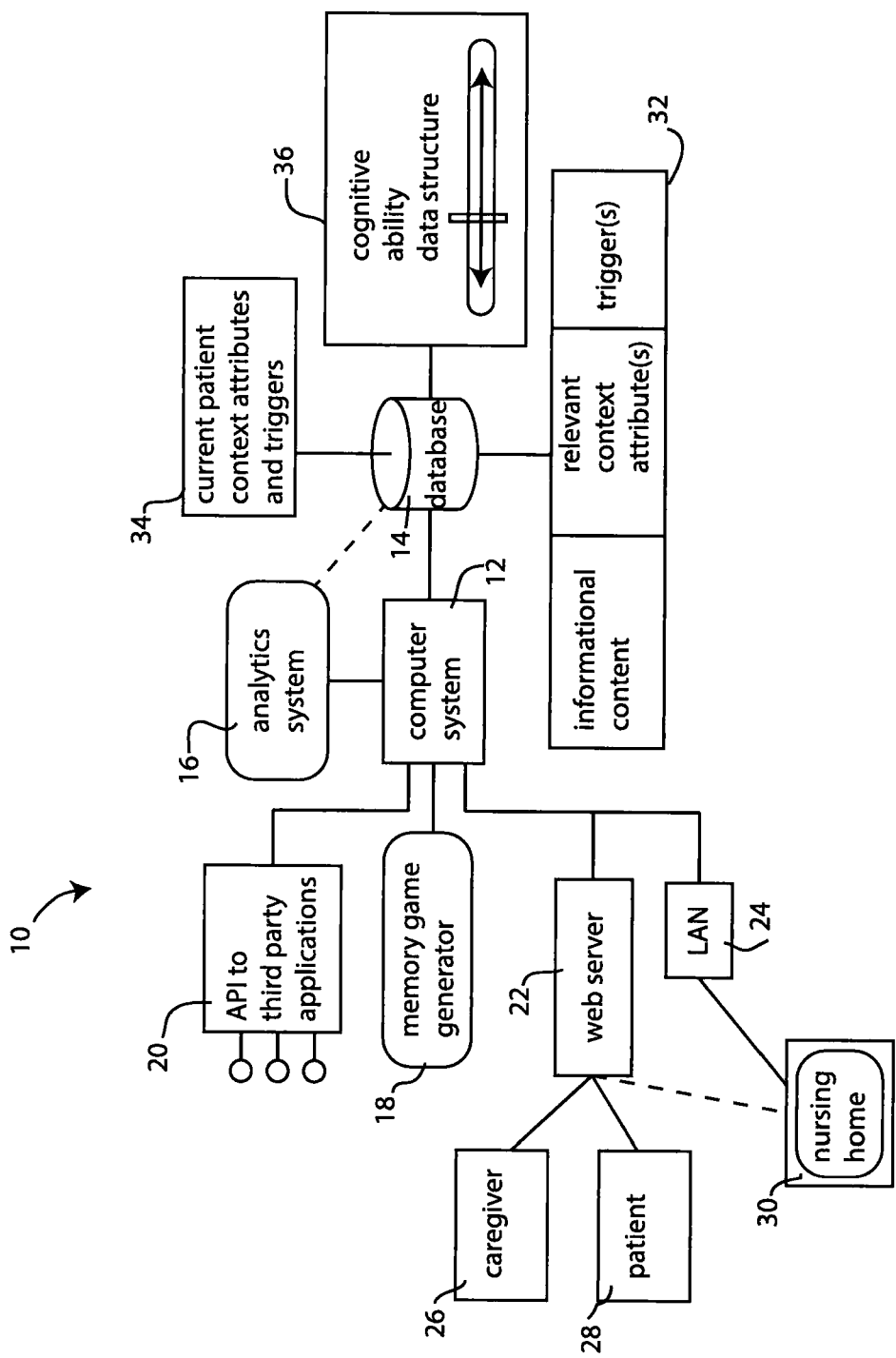
FIG. 33 is a block diagram showing the computer-implemented system and its associated database and data structures.

Referring now to FIG. 33, a computer-implemented system for assisting persons of reduced cognitive ability to manage upcoming events will now be discussed. The computer-implemented system is shown generally at 10, and includes a computer system 12, which may be implemented using a single computer or using a networked group of computers to handle the various functions described herein in a distributed fashion. The computer system 12 manages an electronic database 14 and also optionally an analytics system used to analyze data stored in the database 14. The database 14 functions as a data store configured to store plural items of information about time-based events (and other context-based events) for the patient. The analytics system may be programmed, for example, to analyze trends in a particular patient's cognitive abilities, so as to adjust the performance of the system to match those abilities, and also to provide feedback information about the patient to interested parties such as the patient's caregiver.

If desired, several different presentation devices may be used by a single patient. For example, one device may be a tablet computer operated by the patient, while another device may be a wall-mounted television display in the patient's room. The system can dynamically control which device to use to interact with the patient. In some instances, both devices may be used simultaneously. The system is able to customize the presentation sent to each device individually. Thus the level of complexity for the television display might be different than that used for the tablet computer, in a given situation. The system is able to use context information and also the patient's cognitive ability to adapt each display as appropriate for the patient's needs.

The computer system 12 may also be programmed to generate memory games that are supplied to the patient. Thus a memory game generator 16 is shown as coupled to the computer system. It will be understood that the generator may be implemented by programming the computer system 12 to generate and make available the appropriate memory games, based on the patient's cognitive ability. Memory games can be extremely helpful to exercise the patient's memory, possibly slowing the progress of the patient's disease. In addition, feedback information captured automatically as the patient plays the game is used to gather information about the patient's current cognitive ability, which is used by other systems as will be more fully explained below.

The computer system 12 also preferably includes an application program interface (API) that presents a set of standardized inputs/outputs and accompanying communications protocols to allow third-party application developers to build software applications and physical devices that interact with the system 10, perhaps reading or writing data to the database 14.

The computer system 12 includes a web server 22 by which the caregiver 26 and patient 28 communicate with the computer system 12. In this regard, web pages are delivered for viewing and interaction by computer devices such as tablets, laptop computers, desktop computers, smartphones and the like. The computer system 12 may also be connected to a local area network (LAN) 24, which allows other computer devices to communicate with the computer system 12, such as a workstation computer terminal utilized by a nursing home staff member 30, for example.

The database 14 is configured to store data organized according to predefined data structures that facilitate provision of the services performed by the computer system. The database includes a data structure 32 that stores plural items of information (informational content) that are each associated with a set of relevant context attributes and associated triggers. By way of example, an item of informational content might be a reminder message that the patient has an optometrist appointment. Associated with that message might be a trigger datum indicating when the appointment is scheduled. Also associated with the message might be other context attributes, such as how large the message should be displayed based on what device the message is being viewed upon. See FIG. 32 as an example of a display of this message.

When the appointment is still distant in time, the informational content stored for that event might include a very general text reminder, stored as one record in the data structure 32. As the time for the event draws near, the system might provide more detailed information about the event (such as a reminder to "bring your old glasses"). This would be stored as a second record in the data structure. The system chooses the appropriate item of information, by selecting the one that matches the current context.

In this regard, the system also stores in another data structure, the current context for the patient, such as where the patient is located, any relevant medical condition attributes, and the like. These are shown as context data structure 34. Further details of the context attributes are discussed below.

The computer system 12 uses the current context attributes in structure 34 in determining which information content to retrieve from structure 32.

In addition to the patient's current context, the computer system further maintains a cognitive ability data structure 36 which stores data indicative of the patient's cognitive ability. This may be quantified, for example, as a relative value suitable for representing as a sliding scale, e.g., a 1-10 scale. The patient's cognitive ability may be assessed by explicit entry by the caregiver or nursing home staff. Alternatively, the system can establish the cognitive ability data itself through feedback from the memory game generator 18 or by analyzing how well the patient is able to interact with the system generally.

Figure 23:
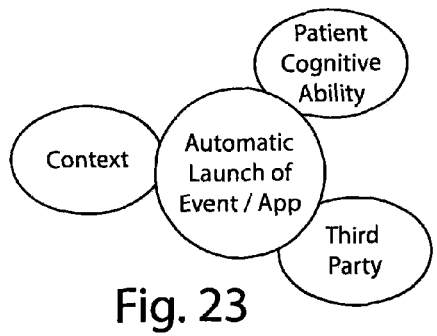
FIG. 23 is an entity diagram illustrating basic components of how an event or application is launched automatically using the disclosed system.

In one embodiment the system automatically launches specific applications and events based on set parameters configured by third parties, taking into account specific information, such as patient context, technology context, and situation context. FIG. 23 shows the key considerations that are taken into account during the process of determining which application/event to launch, when to launch it, and how to launch it. If the context information meets the parameter settings, the execution of an application and/or event is triggered. This provides some information or interaction for an individual to see or use on a computer terminal such as a tablet computer. The system also adjusts the level of interactivity based on the cognitive ability of the patient. The goal is to provide a patient or user a non-intrusive, automatic way to obtain information and services that are relevant and sometimes necessary.

With reference to FIG. 23, the third party is a person or entity that generally has at least some involvement in caregiving. Such third party may have control to put in reminders, start videoconferences, upload pictures, set appointments, and other features of remote care. As used herein, the term "caregiver" refers to such a third party and may include family members, doctors, nursing staff, and the like.

As depicted in FIG. 23, context also provides useful information. The system is able to initiate some of events/applications with knowledge of other factors that the caregiver may not be aware of. These include the situation currently at the nursing home or other patient center (current situation detectable by cameras, microphones, nurse/doctor input, medical sensors, and the like), active/available technology information (e.g., don't send the reminder to the person's watch but put it on the TV), and medical information (data from medical sensors, current doctor reports, current status reports by users).

Cognitive Ability

Patient cognitive ability also forms an important aspect of the system, as shown in FIG. 23. Patient cognitive ability is the current level (on a rating scale) of the patient's ability to interact with the electronics system, tablet, or other device in the system. If the rating is high, the patient likely can interact with the device himself or herself and may not need as much assistance from some context or third-party support. If the rating is low, the system and third parties can provide more support. The cognitive ability scale, and how it is determined, is discussed more in relation to FIGS. 29 and 30 below.

The computer-implemented system captures and stores an electronic data record indicative of the patient's cognitive ability. In one embodiment the electronic data corresponds to a collection of individual measurements or assessments of skill (skill variables), each represented numerically over a suitable range, such as a range from 0 to 10. If desired, an overall cognitive ability rating or aggregate assessment may also be computed and stored, based on the individual measurements or assessments.

The dynamic rendering system uses these skill variables to render facts in the most appropriate manner based on the patient's skill set. In this embodiment the collection of skill variables, stored in memory of the computer, thus correspond to the overall "cognitive ability" of the patient.

The skill variables comprise a set that can be static or dynamic. Some variables are measured or assessed by human operators and some are automatically assessed by the system based on historical observations and sensor data. The following is a list of the skill variables utilized by the system. In this regard, a system may not require all of these variable, and likewise there are other variables, not listed here, that are within the scope of this disclosure as would be understood by those of skill in the art.

Anxiety level
Vision impairment or skills
Short-term memory skills
Long-term memory skills
Recognizing and remembering names/familiar faces
Reading comprehension skills
Attention skills
Time and space sensing
Speech skills
Hearing and comprehension skills
Ability to solve simple logical problems
Inference skill (ability to understand normal implied consequences of actions and facts)

Figure 24:
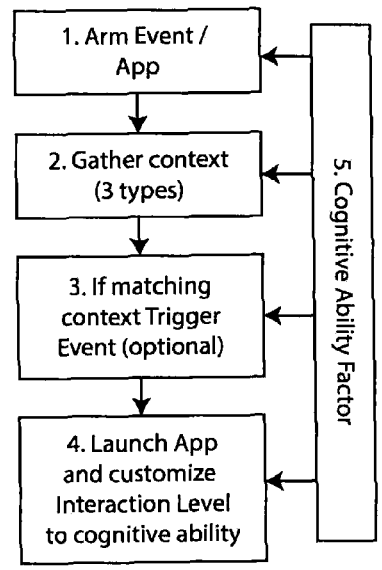
FIG. 24 is a high level flowchart diagram illustrating how cognitive ability factors into the launching of an event or application.

If desired, these skill variables may be algorithmically combined by the computer system to derive a single value "cognitive ability" score. A suitable scoring mechanism may be based on the clinically recognized stages of Alzheimer's disease, namely:

Stage 1: No impairment
Stage 2: Very mild decline
Stage 3: Mild decline
Stage 4: Moderate decline
Stage 5: Moderately severe decline
Stage 6: Severe decline
Stage 7: Very severe decline Context In addition to cognitive ability, the system also takes contextual information relevant to the patient into account. FIG. 24 shows the high-level flow chart for this context-dependent application/event activation for people with various cognitive abilities. (Step 1) A third party (e.g., family, friend, caregiver) will input information and configure the parameters for triggering of events and applications. (Step 2) Once the system has been armed, the system will gather and store contextual information. Such context information, about events and the like, are preferably composed of three sub-contexts: patient related information, situational/external information, and event/application/device information. (Step 3) If contexts meet the armed settings of the system, an event may be triggered. (Step 4) If triggered, the system will launch the application whilst customizing the interaction level for the patient.

In one embodiment the context of an event (an event being an application, task, etc.) can be composed of 3 sub-contexts: a patient-related context, a situational or external condition context, and a technology context. The state of these contexts is stored in a context data structure within the memory of a computer forming part of the system.

The Patient-Related Context

The patient-related context contains all the information that is available from the patient (this is not exclusive). This information is stored as data in the context data structure. Examples of patient-related context data include:

Medical context obtained from sensors (e.g., vital signs)
Digital medical record (history)
Patient behavior (e.g., sleeping or not)
Patient location (e.g., in the room, looking at the display)
Patient preference (e.g., audio trigger/notification preferences, preferences of sounds, videos, tv shows, pictures)
Family/Caregiver wishes The Situational or External Condition Context The situational/external context contains all the information that is available from external sources to the patient (this is not exclusive). This information is likewise stored as data in the context data structure. Examples of situational or external condition context data include:
Weather information
Time
Third party(ies) information (e.g., identity)
Watching TV and what's on
Other people in the patient's room The Technology Context The Event Application/Device context contains all the information that is available from the devices that make up the system. This information, collected by communicating with the devices themselves, is likewise stored as data in the context data structure. Examples of technology context data include:
Status of the tablet display device
Amount of bandwidth available
Type of display (e.g., size)
Type of network
Other devices available (smart watches, TV's in the room, other components in the system)

The technology context is useful because different devices may be added to the network at a future time to add additional functionality. For example, if the patient or patient's caregiver purchased a 'help me' necklace, a new TV, or a digital picture frame, the system can recognize contexts including these new technology (allowing the system to modify its behavior, for example, by displaying the pictures on the picture frame instead of the master tablet device).

Each event/application uses a specific context (subset of the most general context) to be triggered.

Polling Contextual Information

Figure 25:
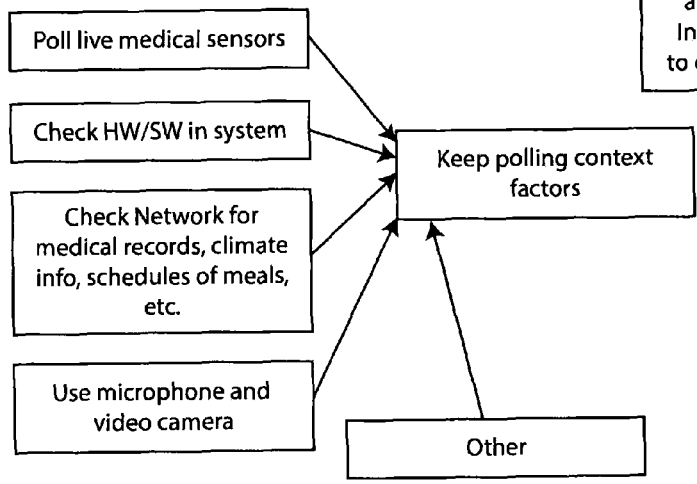
FIG. 25 is a flowchart depicting how context is gathered and used by various components within the system.

FIG. 25 illustrates the polling contextual information that the system will gather from Step 2 of FIG. 24. As previously mentioned, the information will be divided into three categories. Patient-related information, such as medical records, will need to be manually inputted into the system database by a third party. However, live medical information will be constantly gathered by the system via sensors, stationary and mobile.

Figure 26:
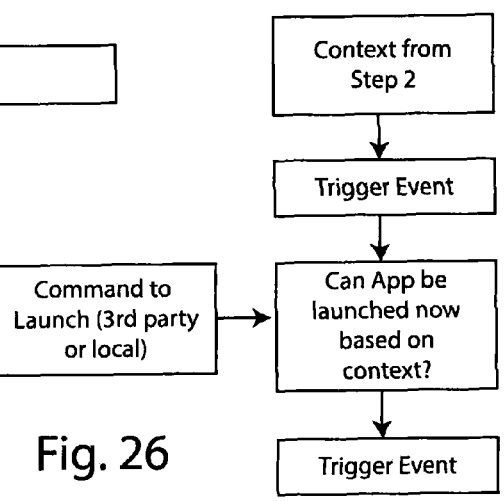
FIG. 26 is a flowchart illustrating the trigger event flow implemented by the system.

Once all contextual information has been gathered, the system will analyze the data to determine whether an event will be triggered based on the parameters set by the third party (FIG. 26). If it is determined that the trigger contexts have been met, then the system will evaluate whether the event will be launched. For example, if the schedule reminder is to go off at a specific time, the system will need to determine whether the patient is present in the room. If the patient is not in the room, the system will not launch the alert; however, if the patient is observed to be present, then the system will trigger the event. Similarly, the system will not launch the alert or event when, for example, a family member wants to engage in a video call, but the context indicates that it is nap time, or that a doctor is currently providing therapy (based on a priority ranking). Likewise, the system would not launch a reminder about medication if the patient is still at dinner and the medication is to be taken after dinner.

Figure 27:
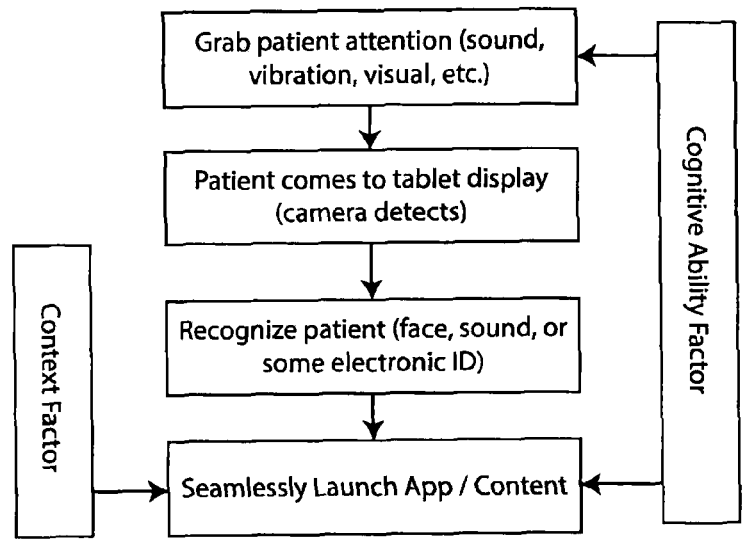
FIG. 27 is a flowchart illustrating the event launch flow implemented by the system.
Figure 28:
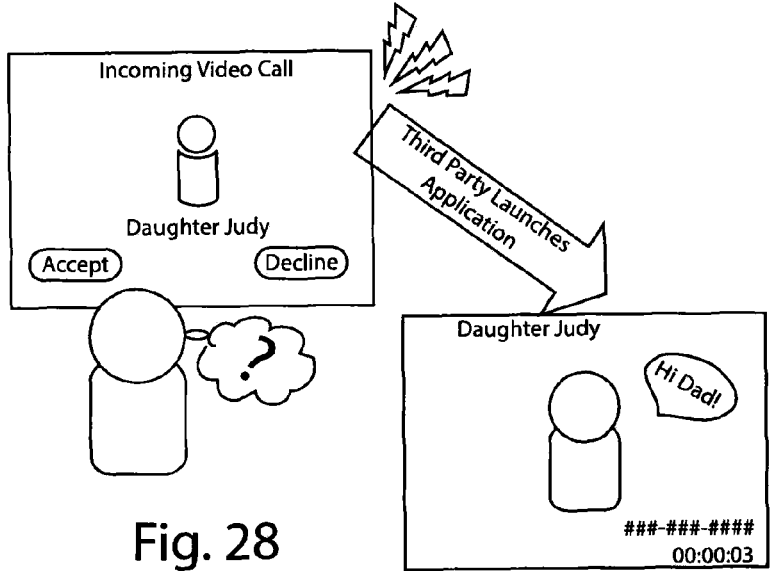
FIG. 28 is a use case diagram showing an exemplary use of the system.

Other examples of trigger events include:
person falls
timed event (e.g., medication/reminder)
sleeping, eating, blood pressure
third-party initiation
another person enters room
voice command As shown in FIG. 27, depending on the patient's cognitive ability, the method of obtaining the patient's attention may be more obtrusive and obvious. The alert will draw the patient towards the tablet display screen, at which time the camera will detect the presence of the patient. If the presence is recognized as the patient (identification may be established by facial recognition, sound or other electronic identification system), the system will seamlessly launch the application/content. Upon launch of the event, the system will again consider the cognitive level of the patient to adjust the level of interactivity and necessity for interpretation appropriately. For example, if the patient is receiving a video call, then the system will alert the patient. If the patient is fully functional, the system will display the options for the patient to either accept or decline the video call. In the case of a low-cognitive patient, the system will authenticate the patient's identity prior to automatically launching the video call or the calling third party could automatically initiate the application, as shown in FIG. 28.

Figure 29:
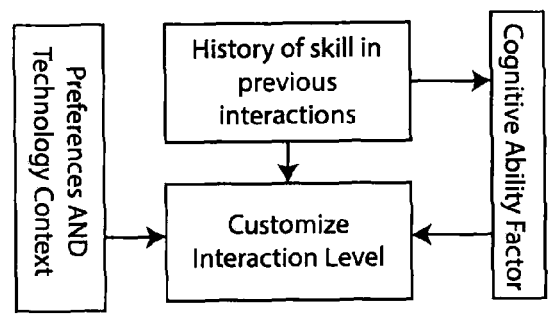
FIG. 29 is an interaction diagram showing how the interaction level of the system is customized based on cognitive ability and based on preferences and technology context information.

When customizing the interface for the patient, the system will take into consideration several factors (FIG. 29). Initially, the cognitive ability of a patient will need to be inputted manually by a third party; however, as the patient continues to utilize the system, the system will register and adapt to the history of skills of the patient from previous interactions. The system also can provide mini-games specifically designed to test the current cognitive ability, and thus the system can automatically update how it should interact with the user.

Figure 30:
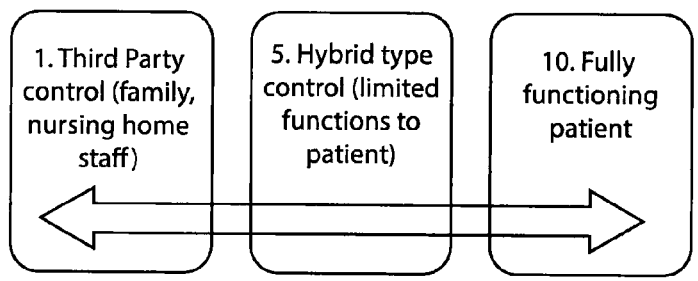
FIG. 30 is a diagram showing how cognitive ability is modeled by the system, as reflected in the cognitive ability data structure maintained in computer memory by the system.

Additionally, the system will apply the preferences of the patient and third-party individuals (e.g., doctors, caregivers, family, friends, etc.). Thus, the patient will not have difficulties using or interpreting the system's events. The interface of the system will change depending on the patient's preferences and cognitive level as well. From a simple and automatic interface for those who are cognitively (or technologically) incapable, to more complex and manual for the independent and cognitively high-leveled patient (FIG. 30).

Adjusting the actual use of applications (not just launching the application but also changing the user interface, buttons and/or modes of interaction) based on determined cognitive ability factor is important to making sure that the application can be useful to the patient.

One embodiment requires manual input of the patient's cognitive level; however, the system will adapt to the patient by having the patient perform tests within the system. The embodiment may be configured to day-to-day differing cognitive levels. The system's parameters can be routinely adjusted by third parties. Alternatively, the system can be configured to perform daily or weekly or bi-weekly testings to automatically accommodate the patient's needs.

Customization of the system is not limited to events launched when contexts are triggered. The system may launch events when in a state of rest. For example, if there are no events set to launch, yet the patient is observed to be present in the room, the system tablet display may go dark or display a picture show or become a reflective mirror.

Figure 31:
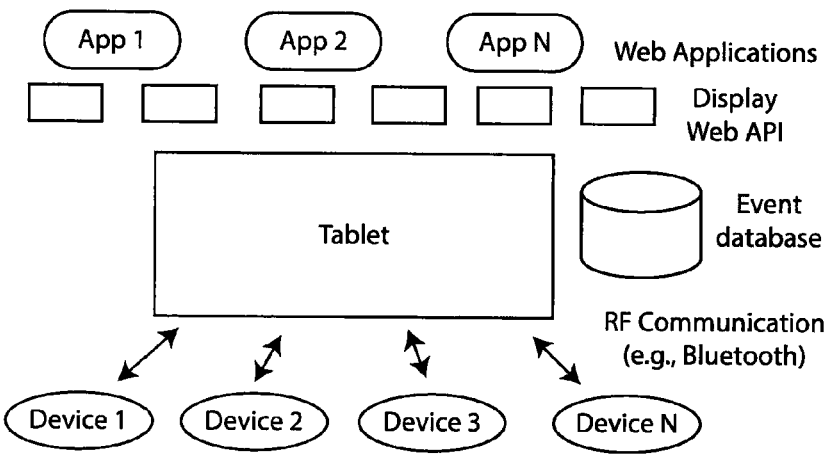
FIG. 31 is a block diagram showing one tablet-based, web-enabled system embodiment.
Figure 32:
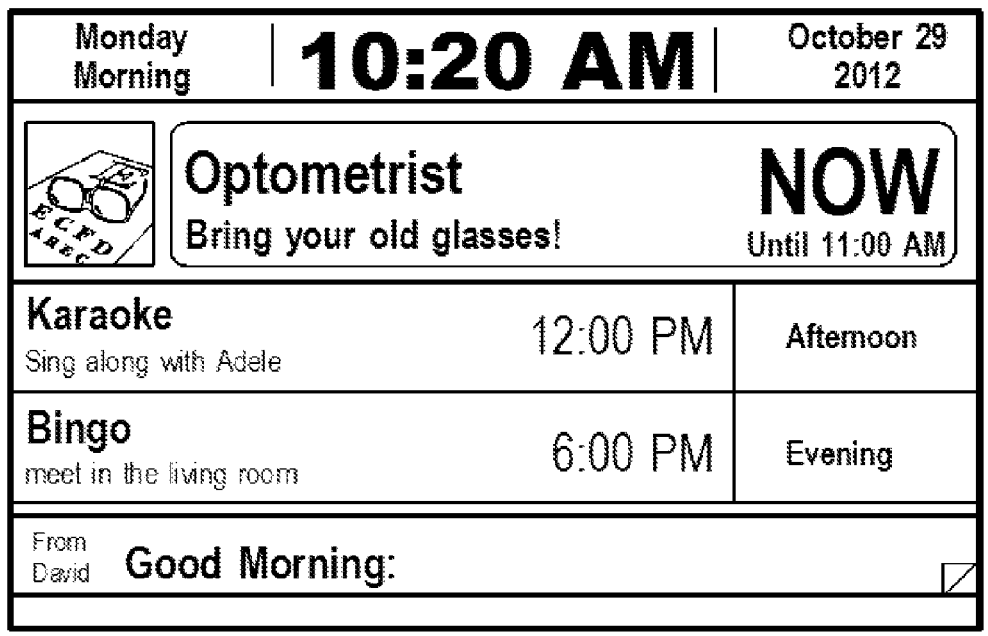
FIG. 32 shows an example screen display with several exemplary applications/events launched.

FIG. 31 illustrates one embodiment in which the system is comprised of the tablet screen, event database, multiple web applications, RF communication (e.g., Bluetooth), and connections to a multitude of devices (e.g., cameras, microphones, speakers, computers, mobiles, etc.). The system will also display Web API. FIG. 32 shows an example user interface that includes applications/events that were launched.

If desired, an additional display can be provided to the caregiver or to another third party. This additional display could be implemented on a tablet or smartphone and would provide information to the caregiver about what the patient is up to and activities he or she did in the past, as well as feedback about the patient's medical condition. This feedback loop provides reassuring information to the caregiver. In general use, this additional display presents information that is different from the information displayed on the device used by the patient. Like the information presented to the patient, the information presented to the caregiver is derived from information stored in the database system, which may be supported by a server associated with a nursing home or healthcare provider, or which may be supported by a service provider offering the services using Internet-based or cloud computing resources.

Additional Explanatory Use Cases

To further illustrate some of the possible uses of the disclosed system, consider the following use cases that are made possible by the disclosed computer-implemented system:

- Video communication initiated by remote third party which is launched when the patient is looking at the display; the attention of the patient can be triggered by an audible signal to bring the patient to the display
- Application triggered by a medical condition based on readings from devices connected through Bluetooth communication (e.g., message to the patient display if the readings show that he is dehydrated)
- Application triggered by the understanding of patient behavior (e.g., patient in the room and not sleeping)
- Activation based on a certain time of the day
- Message displayed on a display depending on external conditions (e.g., based on finding that it is cold outside could warn the patient to wear a warm jacket or emergency message and what to do could be displayed in case of fire)
- Pictures displayed on display if the display does not display other information (thus technology context shows no conflicts and patient context shows time of the day that the person may enjoy pictures)

Priority and Conflict Resolution

When several applications are armed, conflict can happen when several contexts are met at the same time. To solve this issue each application/event is assigned a level of priority. In a case of same priority, the one first entered in the queue is executed.

Figure 34:
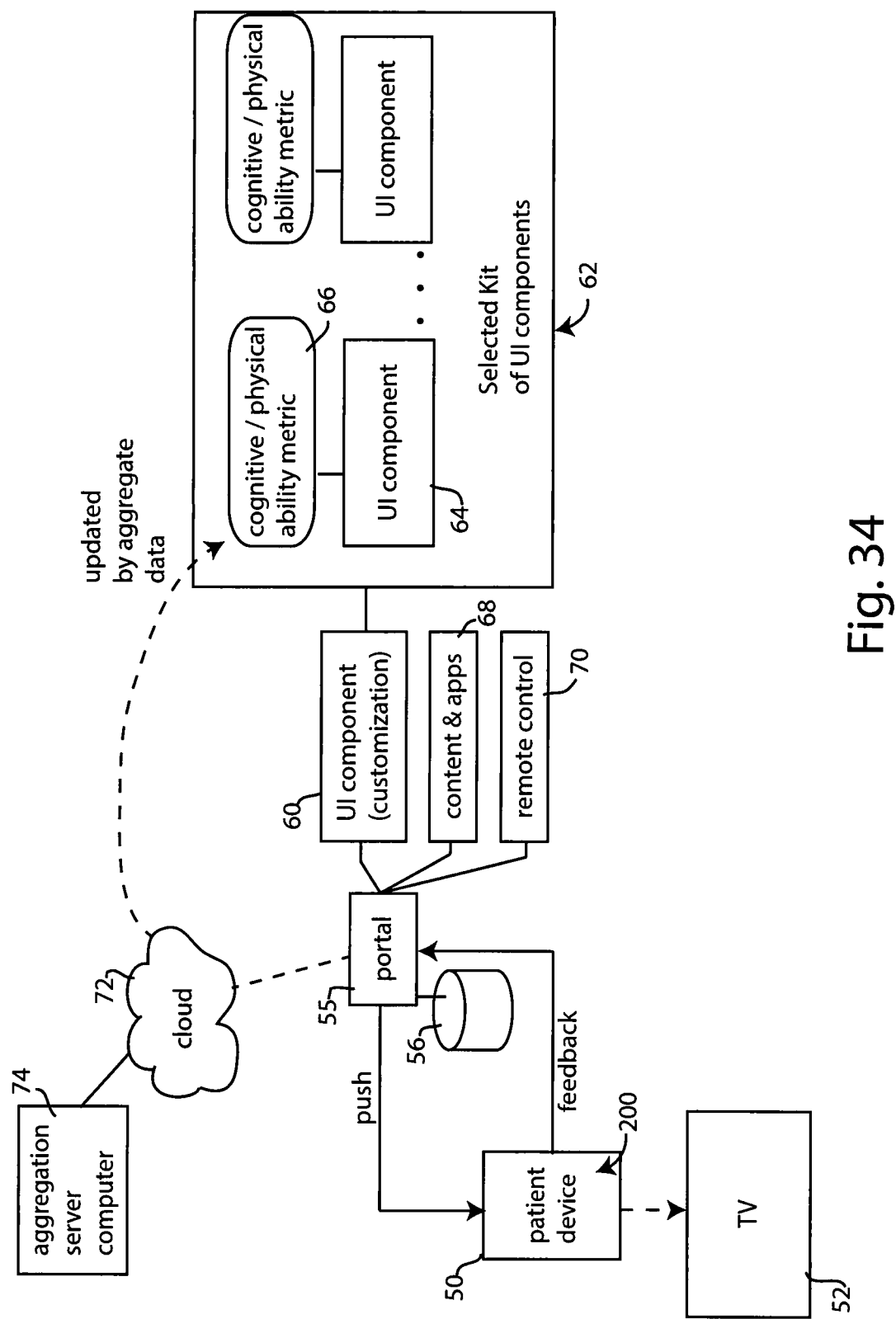
FIG. 34 is a block diagram showing how the patient device and the network-based portal computer are integrated.

Referring to FIG. 34, an overview of the integration between patient device 50 and the network-based portal computer 55 will now be given.

The Patient Device

The patient device 50 with display 200 is configured generally as described above to provide services to a person of reduced cognitive and/or physical ability. The patient device has a communication port, such as a WiFi wireless communication port or cellular data communication port, allowing the device to communicate over the Internet. Alternatively, the information displayed on the device can be sent to a TV 52 in the patient's room. The TV 52 can be provided with computer network communication capability, allowing it to directly communicate with the portal computer 55. Alternatively, the TV 52 can be configured to act as a display that mirrors the information shown on the patient device 50. In this later case, the TV 52 is in communication with the patient device 50 and device 50 handles communication with the portal computer 55.

Figure 35:
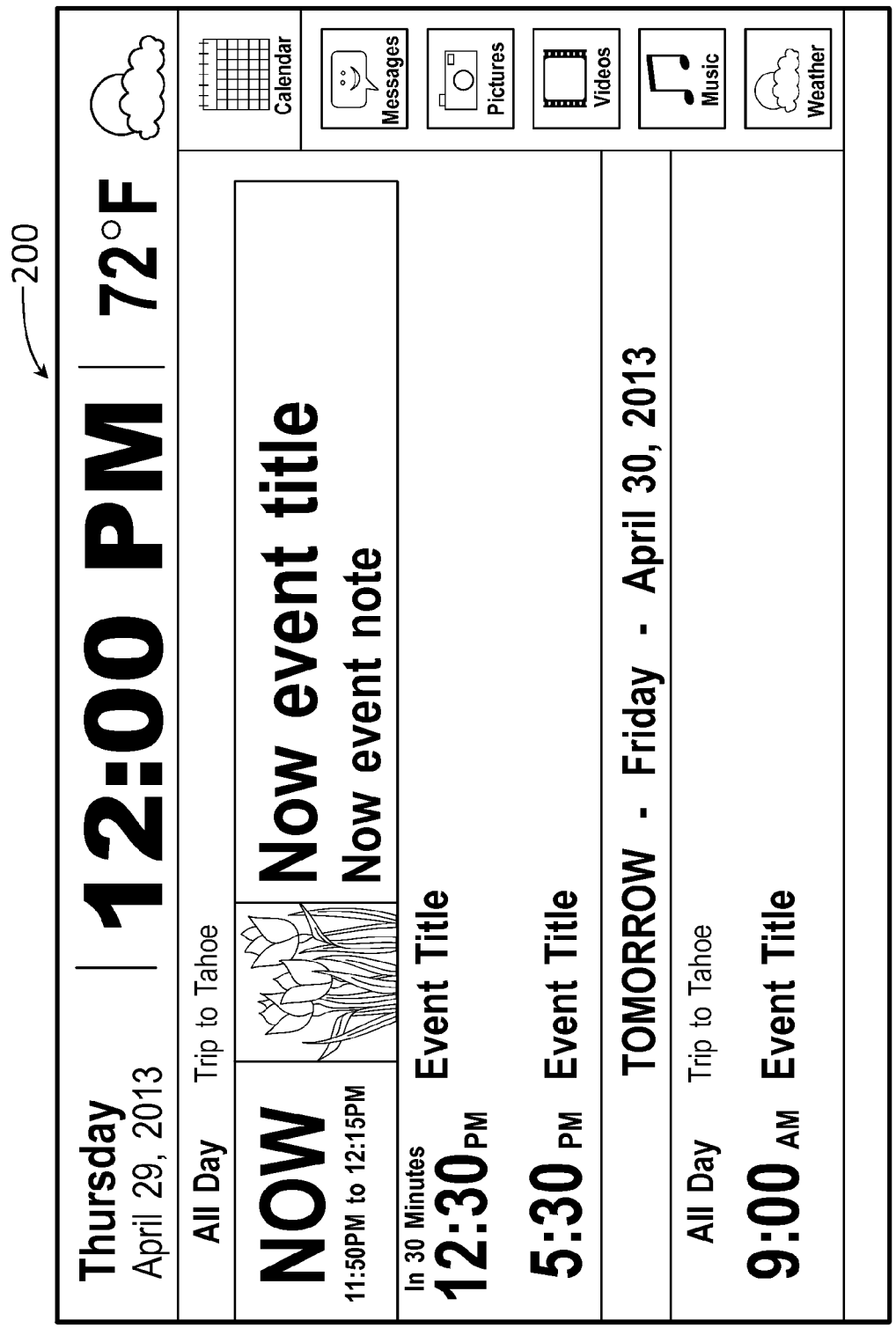
FIG. 35 is an exemplary display screen of the patient device featuring an exemplary calendar application.

FIG. 35 shows an exemplary screen as displayed on display 200 of the patient device. In this case the exemplary screen is generated by a calendar application running on the patient device.

Manner of Programming Patient Device

The patient device may be implemented using a variety of different hardware and software architectures. The tablet form factor is presently preferred.

In one embodiment the patient device may be implemented using a tablet computer using the iOS operating system, the Android operating system, the Windows Surface operating system or other systems. In such implementation, the patient device is implemented as an application (App) running on the native device's operating system (e.g., iOS, Android, etc.).

In another embodiment the patient device is implemented using a tablet computer running the patient device software as a standalone application which includes the hardware interface layers allowing the standalone application to send images to the display 200 and to respond to touch interface commands through a touch screen device associated with the display.

Figure 43:
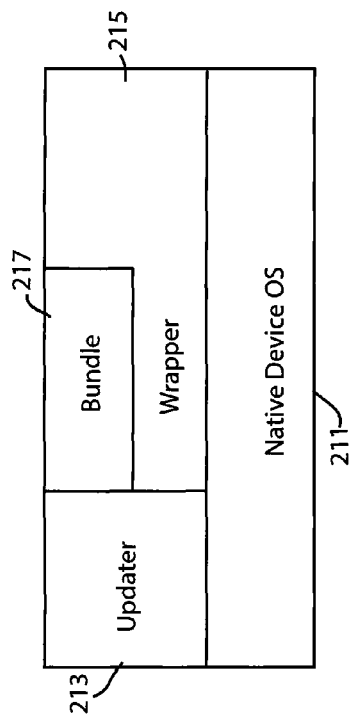
FIG. 43 illustrates the software architecture of the patient device.

The patient device employs the software architecture shown in FIG. 43 by which the processor of the patient device is programmed to perform the functions described here. Of course, different architectures may also be employed. As illustrated, the software architecture may be built upon the native device operating system 231. The updater 213 is a dedicated software component that connects to the portal 55 at a pre-defined time frequency looking for a new wrapper 215 software release.

The wrapper 215 is a dedicated middleware connecting the low-level native device operating system 211 to a UI and application-rendering package. The wrapper 215 implements the device APIs for synchronizing the local buffer to the remote portal 55. These APIs include device authentication; activity, message, picture and video download; user settings and customization download; and check and download the latest bundle 217, including UI design and device-specific applications.

The wrapper 215 executes the code and information provisioned through the bundle 217. The final UI shown on the device is completely customizable depending on the bundle 217 information loaded and the device-specific settings like: zoom level, enabled/disabled apps, volume level, Text-to-Speech enable/disabled; favorite applications; new event prompt options, etc.

The bundle 217 contains all the UI and application-specific code. The system enables very targeted distribution of bundles for each display. With this, it is possible to customize every user interface aspect such as: fonts, creation of new applications, resizing and redistribution of all graphical components.

Thus the bundle contains all event querying and display logic. The wrapper starts bundles, updates bundles and supplies operating system-related functions to the bundle (e.g., text-to-speech, reboot, WiFi restart). The updater allows wrapper updates and starts wrappers.

In implementing this updater-bundle-wrapper configuration, one embodiment based on the Android operating system may be configured as follows.

Updater:

The updater is manually installed on the patient device. The updater provides no visible user interface and normally does not require updates. The updater is started or launched upon booting of the patient device, or it may be started by a user via a suitable touchable icon displayed on the screen of the patient device. Once started, the updater starts the wrapper, if available, and checks for wrapper updates every predetermined time interval, such as every 10 minutes. In case of network failure with no wrapper installed, the updater rechecks at more frequent intervals, such as every minute. The updater installs new wrappers.

Where the native operating system is the Android operating system, the updater may be implemented using the Android APK. An Android service is scheduled to run every 10 minutes through its alarm manager. The Android APK is also used to schedule service run and to start wrapper activity. The APK is also used to broadcast receiver handling onboot message and starting activity.

Figure 45:
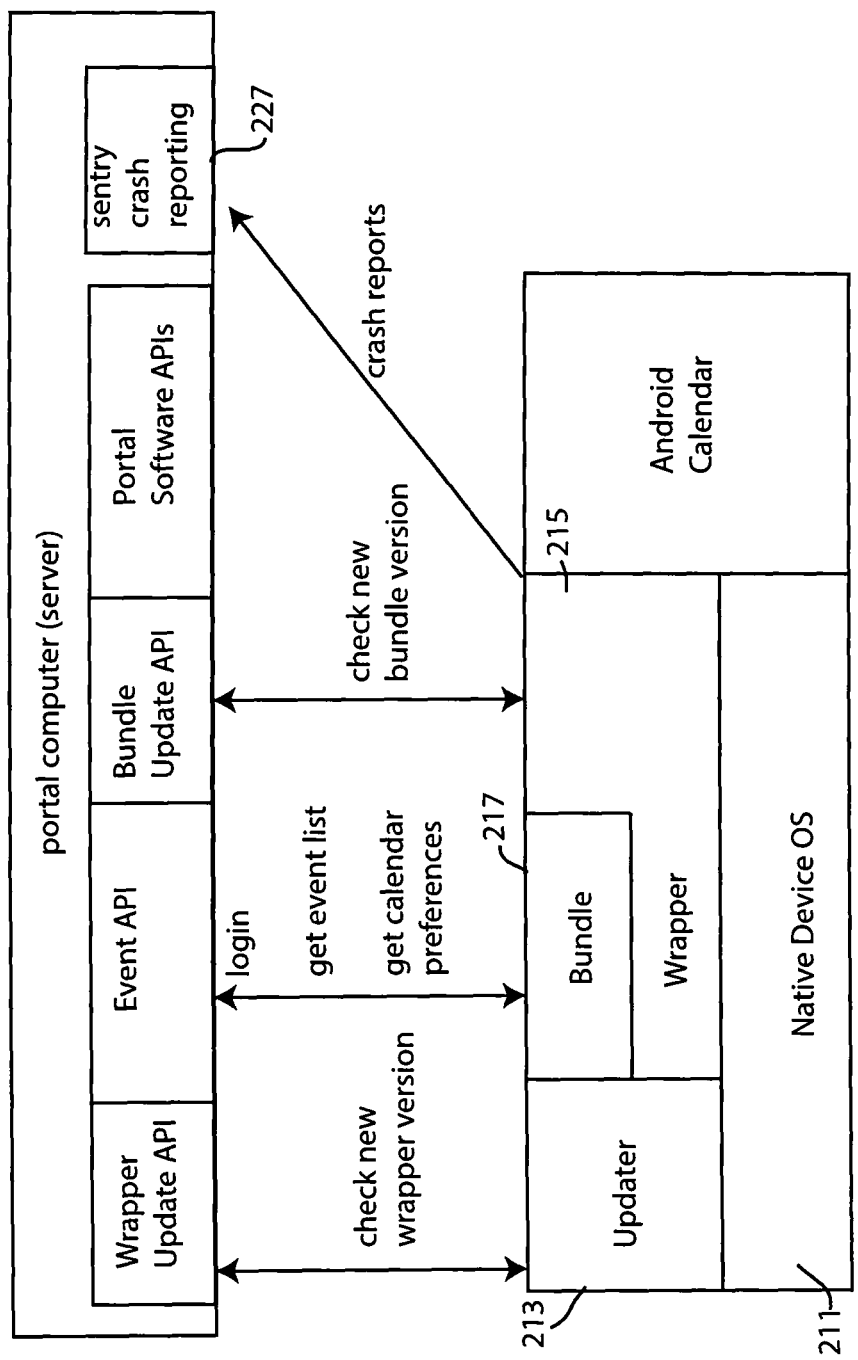
FIG. 45 illustrates the software architecture of the portal device, showing how crash reporting is handled.

Wrapper:

The wrapper is automatically installed by the updater. It has no visible icon and is always started through the updater. The wrapper checks and installs new bundles. The wrapper periodically performs system restart and also periodically performs WiFi restart. These steps are performed to ensure the patient device is forced to reestablish connectivity in the event the network connection is lost for some reason. The wrapper is also responsible for sending crash reporting messages to the portal computer, as shown in FIG. 45.

Bundle:

The bundle is automatically installed by the wrapper. The bundle supports protocols such as HTML5, CSS, JS App. Unlike the updater and wrapper, the bundle is actually visible on the patient device, such as in the form of the calendar. The bundle uses the event API and handles display of all events. The bundle also notifies the wrapper of any display setting changes.

The bundle is implemented in HTML5, CSS, and as a java script (JS) compressed tar file. The bundle may be configured to use and support protocols and technology such as:
 AJAX requests
 Zepto.js
 JQuery (e.g., Internet Explorer only)
 Custom JS communication with TTS and Settings plugins
The following HTML5 APIs are supported:
 Filesystem
 Webstorage
 Audio
 File Writer To further illustrate how the updater-wrapper-bundle mechanism works, refer now to FIGS. 46-50. FIG. 46 shows the updater broadcast receiver operation that runs after the patient device finishes its boot-up sequence. The procedure is straightforward: a start Updater Activity procedure is launched, causing the updater to be loaded and run, whereupon the updater broadcast receiver procedure finishes.

The wrapper is started next, as shown in FIG. 47. The procedure first sends crash reports, if any, testing to ensure the report transmission was transmitted okay, and then deleting the local copy of the crash report. The procedure then tests to see if root access to the underlying hardware is operational, and if not, a report to the user is generated and the wrapper activity start sequence is terminated. This report to the user is provided for troubleshooting purposes; the ordinary user of the patient device is not expected to understand this message.

If root access is successfully engaged, the wrapper activity start procedure then disables the device auto update, schedules a WiFi reboot, restarts and then runs the downloader. Changed settings will also initiate a reboot, as illustrated.

The downloader activity of the wrapper is illustrated in FIG. 48. If there is no new bundle to be downloaded, the wrapper activity merely sleeps for a predetermined time interval and then tests again to see if a new bundle is present. If so, the bundle is downloaded and the activity downloader checks to see if the file was properly downloaded, including checking the file's MD5 checksum to ensure that the downloaded code was not corrupted during transit. The code is then installed and the procedure again enters a sleep state for the predetermined time interval. If any of the downloading procedures or subsequent testing and loading procedures fail, the activity downloader enters a sleep state for a different predetermined interval (the sleep-upon-failure interval).

Figure 49:
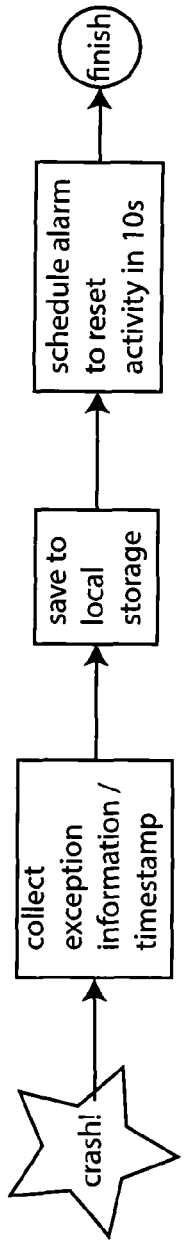
FIG. 49 illustrates the software architecture of the portal device, showing the wrapper activity crash.

The crash handling wrapper activity procedure is shown in FIG. 49. Upon the occurrence of a crash, the wrapper collects relevant exception (error) information, including a timestamp when the crash occurred. This exception information is saved to local storage and an alarm is scheduled to cause the device to restart after a predetermined time, such as 10 seconds. Often a crash or exception may be due to an intermittent loss of network connectivity. Thus a scheduled reset is programmed into the crash-handling procedure to address this by rebooting.

Figure 50:
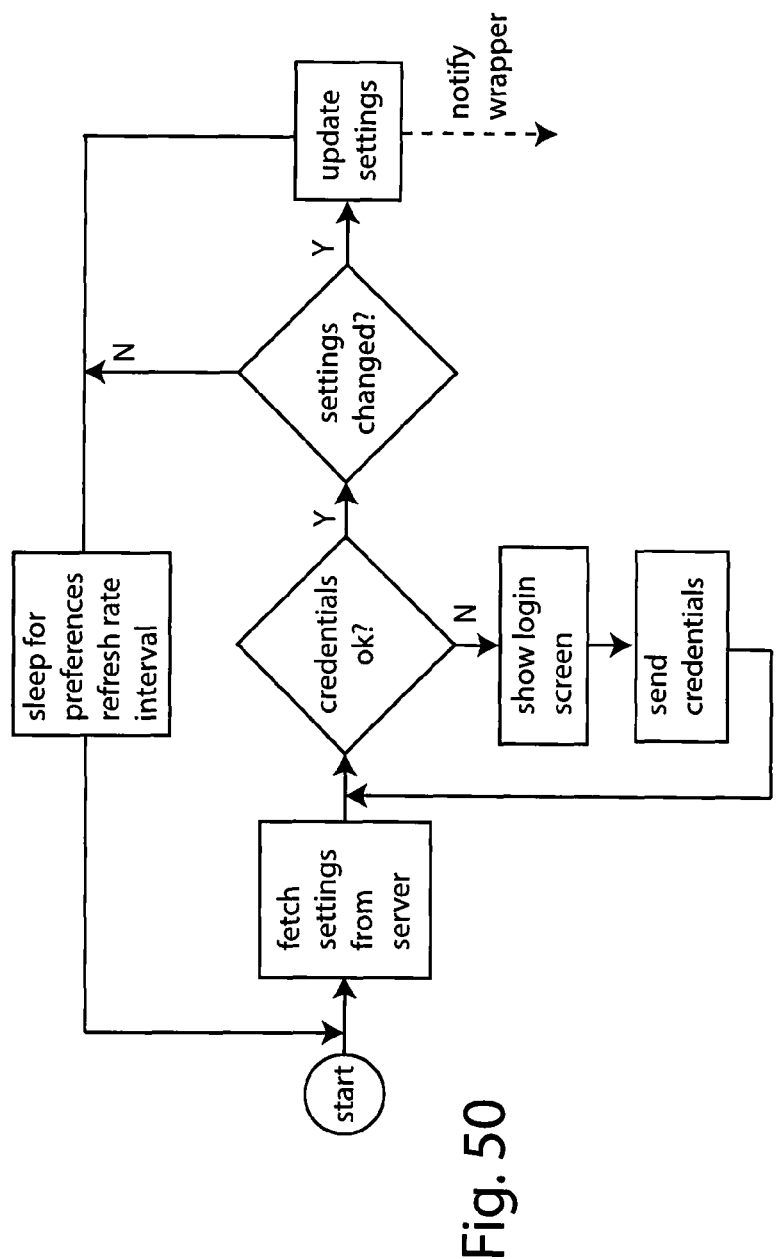
FIG. 50 illustrates the software architecture of the portal device, showing the bundle settings update.

The procedure used by the bundle mechanism is illustrated in FIG. 50. This procedure is run by the bundle on the patient device when settings are to be updated. The procedure fetches the new settings from the portal computer (server), tests to ensure that the portal computer has associated proper credentials with the new settings (to ensure these new settings are intended for this device), and then a check is made to determine if any settings have actually been changed. If so, the settings are updated and the wrapper code is notified. In checking credentials, if the patient device has previously been provided with the necessary credentials, nothing needs to be done by the user of the device. If, however, the credentials are not present, or if they do not match the designation from the portal computer, the user is prompted with a login screen to enter the necessary credentials. In checking the specifics of the update, if the bundle settings update procedure determines that no changes to the settings have been made, the procedure enters a sleep mode for a predetermined refresh rate interval.

By way of non-limiting example, the following refresh rates may be established. All of these may be programmatically changed by interaction through the portal.

| | |
|---|---|
| Refresh rate | 5 minutes |
| Preference Refresh rate | 10 seconds |
| TTS Enabled | Disabled |
| Software Update rate | 12 hours |
| Failure rate | 10 minutes |
| Reboot rate | No reboot |
| WiFi Restart rate | No restart |

Settings Management

In the above table, the following settings may be changed or configured using the portal computer.
 Refresh rate: calendar events refresh from the portal computer (server)
 Preferences refresh rate: settings refresh from the portal computer
 TTS Enabled: enable/disable application (e.g., calendar) text-to-speech
 Software update rate: bundle update check rate
 Software update failure rate: bundle update check rate in case of failure and no calendar
 Reboot rate: periodic reboot rate
 WiFi restart rate: periodic WiFi restart

The Portal Computer

The portal computer is a networked computer or collection of integrated computers that communicate over a suitable network connection with the patient device 50. For example, the portal computer and the patient device may be programmed to communicate over a secure channel via the Internet, such as using a virtual private network (VPN) connection. Associated with the portal computer is a data storage system 56 that is programmed to function as a database into which is stored the data used to implement the patient device-portal integration. If desired, the portal computer can be implemented using the computer system 12 (or server 150 and database 160) described above. Alternatively, a separate computer may be used to implement the portal computer 55.

Family members (or staff in the caregiving facility) interact with the portal computer to customize the user interface of the patient device 50, to select specific content or specific applications, and to directly control the patient device by remote control. Information entered through the portal computer is pushed to the patient device 50, and feedback about how the device is being used by the patient is sent back to the portal computer.

In general, the portal computer 55 stores within its data storage system 56 a collection or kit of UI components as well as digital content (e.g., pictures, video, music) and application programs that can be pushed to the patient device 50 where the application programs are then run. To do this, the portal computer 55 thus functions to allow family members or caregiving facility staff to customize the way the patient device functions. Such customization may be classified into three categories: UI component customization, shown diagrammatically at 60, content and application customization, shown diagrammatically at 68, and remote control capability, shown diagrammatically at 70.

Customizations, including selected UI components, applications and content, are pushed from the portal computer to the patient device. The portal computer assembles a package containing the data structures that store all UI component setting information and certain application selection information. The package may be compressed using any of a variety of different data compression algorithms and then sent via the secure channel to the patient device. The patient device decompresses the package and extracts the included component setting information and application selection information. These data are then placed into a buffer in memory of the patient device while the current settings of the device are saved in the memory of the patient device for backup. Then the data placed in the buffer is swapped for the current component settings and application selection settings, and any executing applications are commanded to reboot or otherwise reload the new settings.

The data package can also contain actual copies of executable applications to be run on the patient device, as well as content such as pictures, music, video and other multimedia content supplied by the family member. Because the portal computer saves the state of the patient device, the portal computer does not resend copies of executable applications that, according to the saved state information, are already resident on the patient device. When a family member or other caregiver selects to suppress or delete a particular executable application from the patient device, an application selection setting is stored in the package delivered from the portal computer to the patient device. This application selection setting is operated on by the patient device by suppressing visibility of the executable application, and without actually deleting the application from the patient device unless it is deemed necessary to reclaim storage space from the patient device. Thus if the family member or caregiver later decides to re-enable the application, it can simply be switched on via the application selection setting and does not have to be pushed again to the patient device.

Manner of Programming Portal Computer

The portal computer may be implemented by a networked computer that is coupled to communicate over the Internet. The portal computer has at least one processor and associated non-transient memory into which the program instructions are stored to cause the portal computer to implement the functions described here. Preferably, the portal computer is equipped with display monitor and suitable input device(s) such as keyboard, mouse and/or touch screen.

The portal computer employs the following software architecture by which the processor of the portal computer is programmed to perform the functions described here. Of course, different architectures may also be employed.

Figure 44:
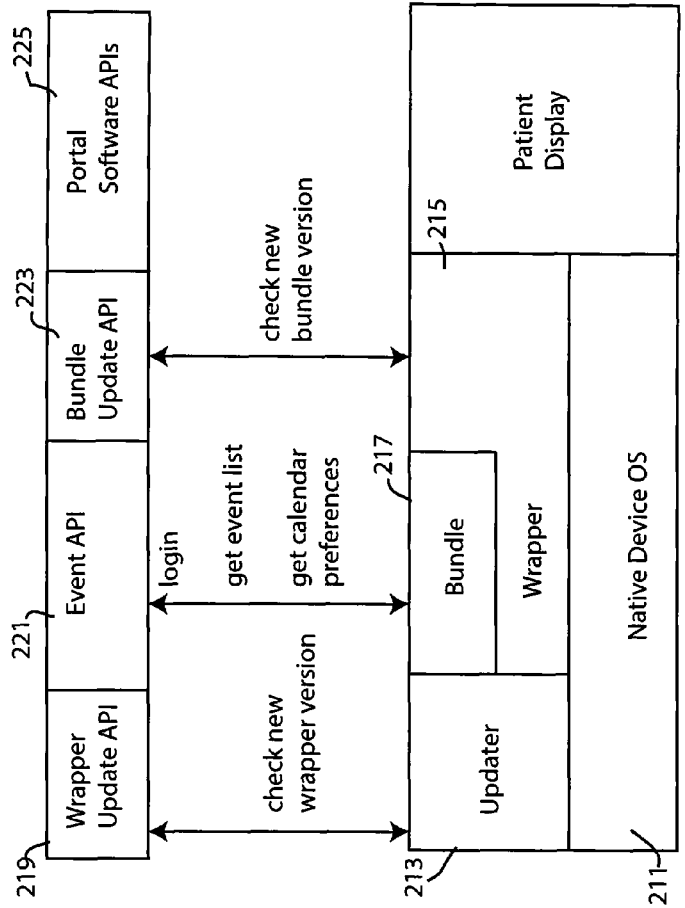
FIG. 44 illustrates the software architecture of the portal device, showing how the portal device communicates with the API of the patient device through messaging.

The portal communication software architecture is shown in FIG. 44. As illustrated, the networked computer acting as the portal computer sends and receives messages to and from the patient device. FIG. 44 shows how the APIs of the portal computer and patient device are configured to interact through this messaging. A further description of the portal software API will now be described.

As shown in FIG. 44, the portal computer is configured to include a wrapper update API 219 that communicates with the updater 213 on the patient device, and mediates the "check new wrapper version" message used to signify when a new wrapper is to be delivered and installed on the patient device. The portal computer also includes an event API 221 that mediates events performed on the patient device. The event API responds to messages including "login," "get event list," and "get calendar preferences." The event API also handles similar messages with other applications pushed to the patient device. The portal computer further includes a bundle update API 223 that mediates the updating of bundles on the patient device, through the "check new bundle version" message. Finally, the portal computer includes additional portal software API's 225 by which the portal computer can be interfaced with other systems, such as with cloud services available on the Internet.

Referring to FIG. 45, the portal computer also includes a sentry crash reporting module 227 that logs crash reports sent from the patient device. Such crash reports may be generated, for example, if the previously described updater-wrapper-bundle mechanism does not properly operate, such as due to an intermittent loss of network connectivity. Crash reports may also be sent from applications running on the patient device, such as the calendar application, for example.

Portal Software API Description

Login—

Provide a way to authenticate the client on the server. Once authenticated, an APIKEY is returned. This key will be used as an authentication for almost all other methods.

Params:
username: The Resident Display Login, obtained in the Resident's Display tab;
token: The Resident Display Password, obtained in the Resident's Display tab;
uhid: A UNIQUE hardware identifier. The system accepts only one device per user and vice-versa.

Log Out—
This invalidates the previously acquired APIKEY.

Params:
apikey: The APIKEY obtained with the /login method.

get_update_version—
Returns the latest available bundle version for this client.

Params:
apikey: The APIKEY obtained with the /login method.
get_wrapper_update—
Returns the latest wrapper version to download. In this case, the client UHID is used instead of the APIKEY as identification. At this point, the client is not logged in yet.
Params:
uhid: A UNIQUE hardware identifier. The system accepts only one device per user and vice-versa.
Sync_Api—
Provides all data needed by the client. This includes settings, events, messages and other media resources (photos, music and videos). Every request to this method returns a SHA1 Hash in a header field named E-Tag.
This hash shall be used on the next request. The server uses this information to determine if there was any change in the previously served content. If positive, new data will be returned with a 200 status code. If negative, a 304 will be returned. This not only reduces the server CPU usage but also saves bandwidth.
The media resources (images, music and videos) shall be stored locally. Each media has a unique name across the system.
Accept: Can be used to indicate the desired response format.
On4-Token: The APIKEY obtained with the /login method.
On4-Version: The application version.
On4-TzOffset: The time difference between UTC time and local time, in seconds. A minus sign must be used if local time is behind UTC.
On4-Position: The device latitude and longitude. This information is used to provide accurate weather information to the device.
On4-Time: The current UTC timestamp. The value 0 (zero) is accepted for NOW. The server will return events from this time up to 3 days ahead.
If-None-Match: The E-Tag value obtained from the last request, or empty if first call or none has been provided.

UI Component Customization and Ability Metrics

The user interface with which the patient interacts when using the patient device 50 is comprised of a kit of UI components 62 that can be selected by the family member (or staff member) and then pushed to the patient device. The UI components are stored in the data storage system 56 and comprise a specially chosen set of user interface components, each graded to match a certain level of cognitive and/or physical ability, to provide the patent with the information he or she needs on a daily basis and to allow family members and the patient to stay in touch.

To make it easy for the family member or nursing staff to select the appropriate UI components for a given patient's needs, each of the individual UI components 64 within the kit 62 has at least one associated cognitive and/or physical ability metric 66. The ability metric assigns a numerical score to each UI component based on the degree of difficulty a user will have in using that UI component. The kit 62 includes a variety of redundant or function-overlapping UI components, ranging from automatic, to extremely easy to use, to sophisticated to use, so that the appropriate one can be selected for the particular patient's abilities.

If desired, plural metrics can be associated with each UI component. Thus in addition to a cognitive ability metric, physical ability metrics (vision, hearing, manual dexterity) may also be associated. Cognitive ability and other ability metrics may also be applied to rank the degree of difficulty of different applications or even content, where applicable.

For example, a user of high cognitive ability and high physical dexterity might have no difficulty understanding how to use a dropdown menu UI component to select which photos he or she wants to view in a photo-viewing application. A person of lower ability might not be able to navigate a dropdown menu, but might be able to understand how to use forward and backward buttons to browse through photos once they have been automatically selected for the patient. A person of still lower ability might be unable to operate any UI components, in which case the application would perform an automatic slideshow, where photos are selected at a predefined rate not controlled by the patient.

Figure 36B:
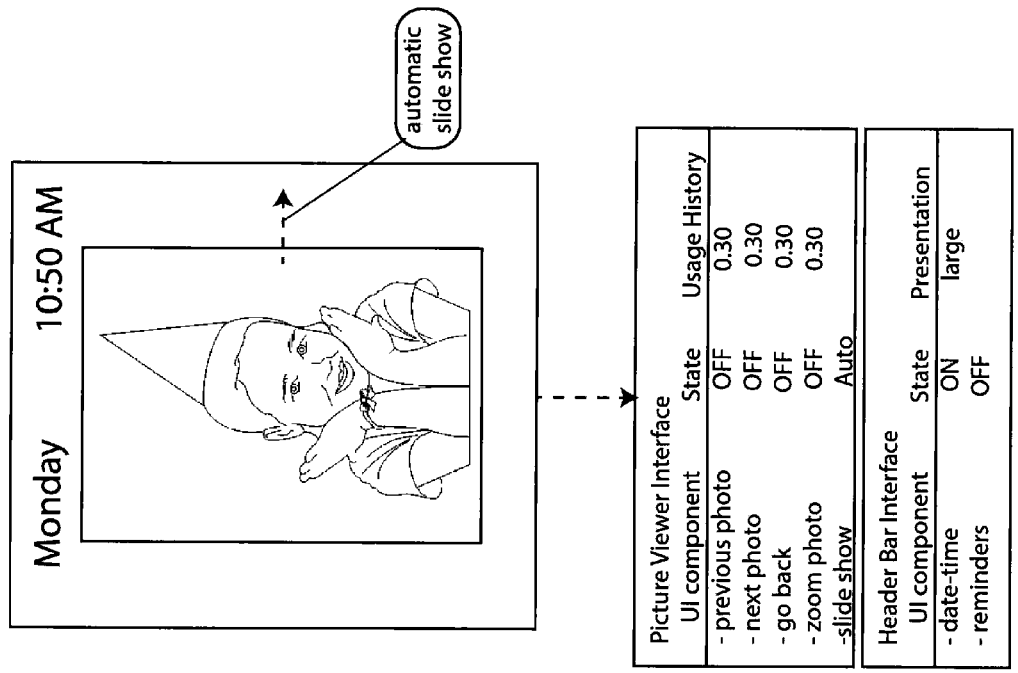
FIGS. 36a and 36b are user interface and data structure diagrams showing how customizations are pushed to the patient device and how usage data are collected.
Figure 36A:
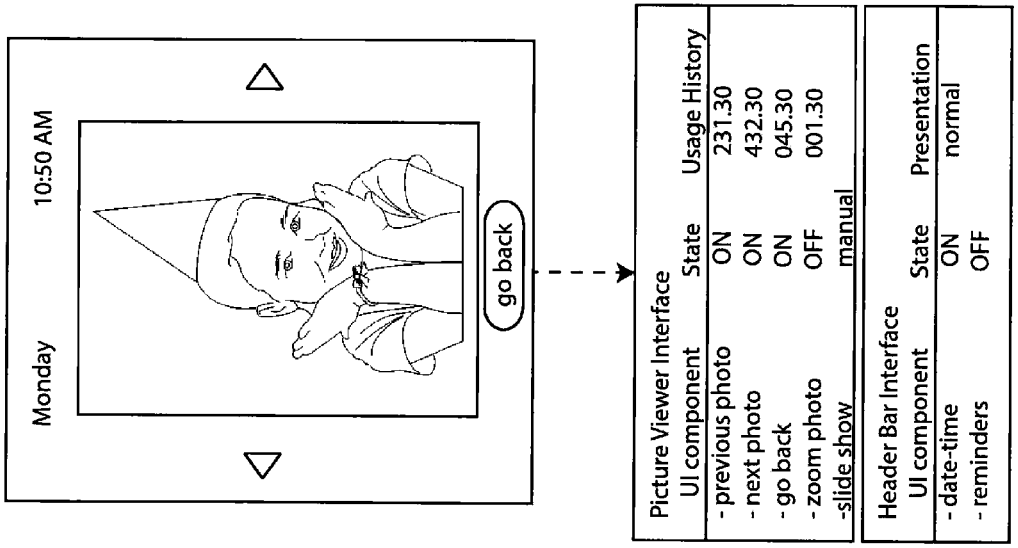

This has been illustrated in FIGS. 36a and 36b, which feature a rudimentary photo-viewing application that has been pushed to the patient device. FIG. 36a represents a display that might be customized for a patient of average eyesight and moderate cognitive ability. Thus in FIG. 36a, the day and time are displayed in "normal" sized letters and the "next photo," "previous photo" and "go back" buttons 80 are displayed and active. For this patient, the prospect of pushing a left-pointing button to "go back" and a right-pointing button to "go forward" is not a daunting task.

By comparison, the user interface in FIG. 36b has been customized using the portal for a person with below average eyesight and limited cognitive ability (or perhaps limited manual dexterity). Thus the day and time are displayed in a "large" size and the "next photo", "previous photo" and "go back" buttons have been suppressed. To account for removal of buttons 80, the slideshow feature 82 of the photo-viewing application has been switched to "auto" which causes the pictures to cycle automatically from a first picture, to a next picture, and so forth. In this case the patient has only to watch the screen. There are no buttons to push.

Use of Cognitive Ability and Other Ability Metrics

By providing a full-featured kit of UI components, the portal computer 55 can selectively assemble a highly refined and highly customized user experience for each patient. However, having this large number of different UI components at different ability metric levels is not without its difficulties. The typical family member or nursing staff person may have little or no experience in user interface design.

Figure 42A:
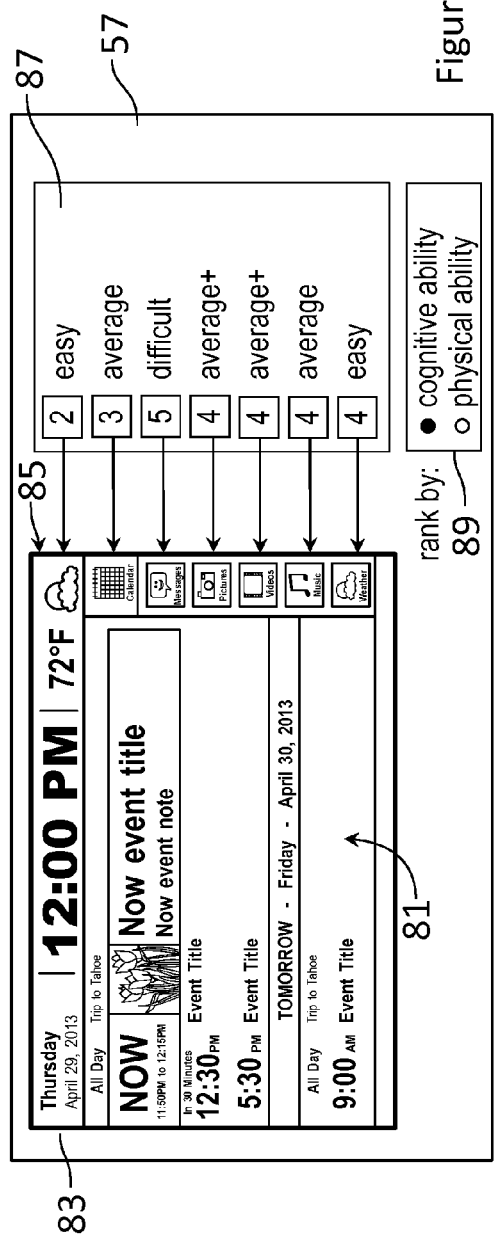
FIGS. 42a and 42b illustrate two different embodiments for displaying ability metrics in association with applications or UI components, the display being presented on the display of the portal computer for use in customizing the patient experience when using the patient device.
Figure 42B:
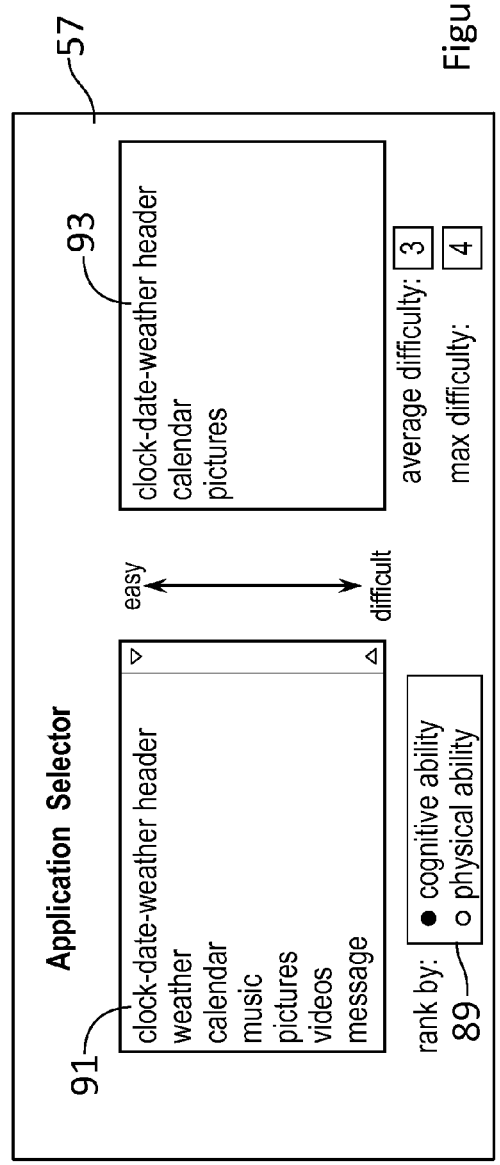

Thus to simplify the UI customization process, the portal computer sorts and ranks UI components according to cognitive ability metric (and other metrics), so that the appropriate ones are offered first to the person seeking to customize the user interface of the patient device. FIGS. 42a and 42b show two alternative embodiments for how this is accomplished. In FIG. 42a, the display 57 presents an image of what appears in the display of the patient device, in this case the calendar application, as at 81, with clock-date-weather header, as at 83. Along the right-hand side of the patient device display is an application selector 85, where icons corresponding to the applications are available to be pushed to the patient device. The display 57 also includes a ranking window 87 where the ability metric for each application is displayed. Note the clock-date-weather header has a metric of "2" indicating that this interface component is relatively easy to use, as compared with the pictures application, which has a metric of 4 and is thus above average in difficulty. As will be appreciated, the ranking window shows metrics as they are assigned by the system, which can either be based on actual usage statistics of the particular patient, or based on aggregate statistics generated by the aggregation server computer 74 (FIG. 34). If plural different metrics are implemented (e.g., cognitive ability and physical ability metrics), the user of the portal computer allows the family member or nursing staff to switch between metrics by selecting the appropriate radio button at 89. Selecting either of these buttons will switch the ranking of the displayed applications to reflect the selected choice.

FIG. 42b shows a different manner of offering applications for selection to be pushed to the patient device. In this embodiment an application selector window 91 lists all available applications, sorted in order of ability metric, based on the radio button selection of the desired metric at 89. The family member or nursing staff can then drag selected applications into the push window 93. Doing this marks the applications in the push window as applications that will be pushed to the patient device. In this case three applications have been selected. The portal computer displays the average difficulty and maximum difficulty based on the applications that have been dragged into the push window. This allows the family member or nursing staff an easy-to-understand grasp of the degree of difficulty the selected pallet of applications will present to the patient.

Alternatively, the portal computer 55 is programmed to automatically select an appropriate configuration, based on previously obtained knowledge of the patient's abilities. This a priori knowledge is obtained through feedback of usage statistics from the patient device, as will be described below.

Figure 39:
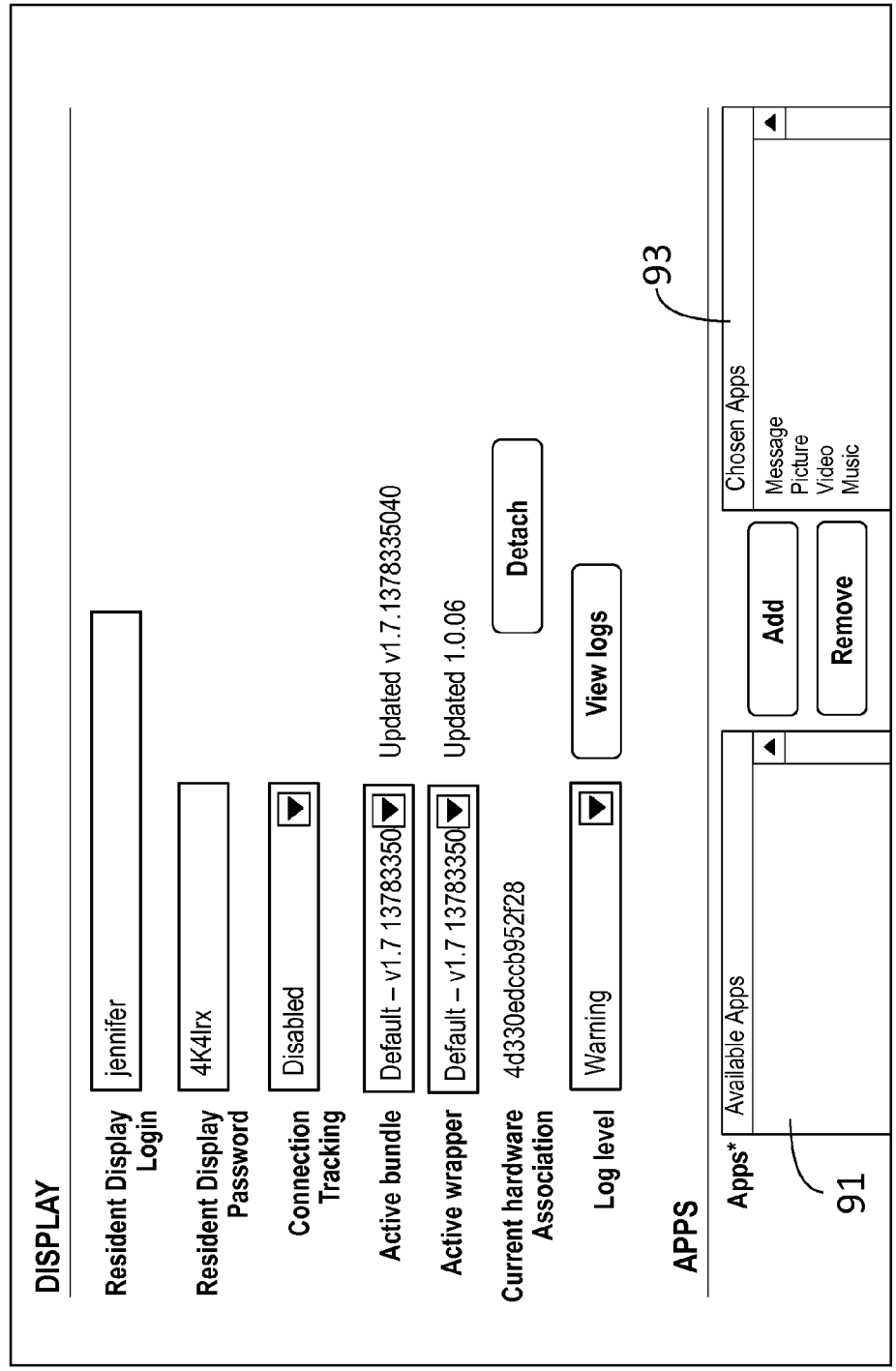
FIG. 39 is an exemplary display screen generated by the portal computer with which settings of the patient device are customized and applications to be pushed to the patient device are selected.

Once the basic selections have been made as to application selection, the portal also provides more detailed screens whereby the family member or nursing staff can configure further details that are specific to the particular application. In this regard, FIGS. 38 and 39 show exemplary screens whereby the basic display and user interaction features are set. FIG. 39 includes an application selection structure 91 and 93, similar to that of FIG. 42b. FIG. 40 shows another exemplary screen that is used to add music and video content to a list of content pushed to the patient device. FIG. 41 shows an exemplary screen used by the family member or nursing staff to preset a messaging application, such as Skype, with persons with whom the patent wants to regularly communicate.

Remote Control

In some instances, a family member may want to share an application or content with the patent, but the user interface for that application or content may be above the patient's cognitive ability. In such case the portal provides a remote control capability, allowing the family member, operating through the portal, to directly control what is presented on the patient device.

For example, during a telephone call or video chat via the patient device, the family member my want to show the patient some pictures that were previously pushed as content to the patient device. Using the remote control capability, the family member could, for example, directly launch a slide presentation application, allowing the patient to see the pictures.

Usage Data Collection, Feedback and Aggregation

Important to the patient device-portal computer integration are the concepts of usage data collection and feedback. Data are collected, in real time, as the patient uses the patient device, noting which applications and content have been viewed and when, and also noting which UI components were used and when. These collected data are then communicated to the portal computer as feedback.

Figure 37A:
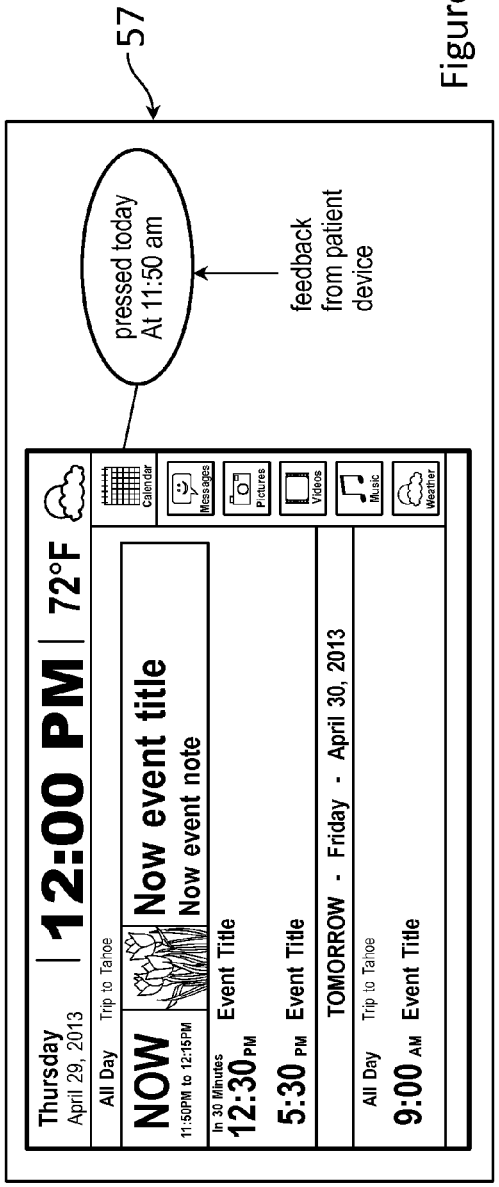
FIGS. 37a and 37b are comparative displays produced by the portal computer, showing how usage feedback from the patient device may be displayed.
Figure 37B:
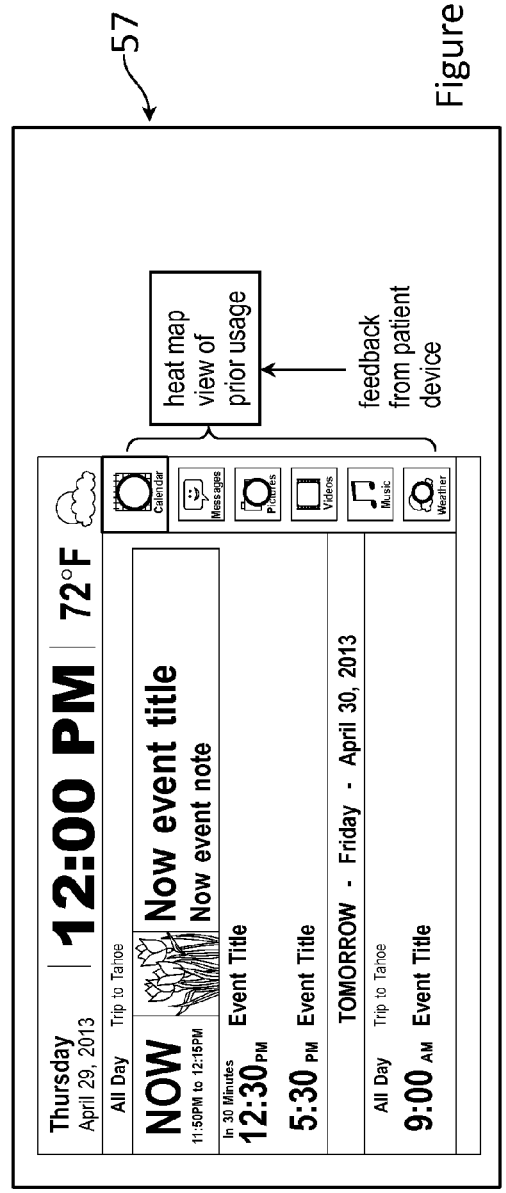

Feedback is important in several respects. First, feedback alerts the family member when a particular user interface component, content or application is not being used, or is being used incorrectly by the patient. This allows the family member to make customizations so as to better match the user interface, content and applications to the patient's cognitive ability. As shown in FIGS. 37a and 37b, the feedback provided from the patient device can be presented to the family member in a variety of ways. Two ways have been illustrated.

In FIG. 37a, the display 57 attached to the portal computer supplies an image of the screen, as it appears on the patient device. This display is updated in real time and shows what the patient is currently doing. In this case, the patient last pushed the "calendar" button and is thus viewing the calendar application. FIG. 37b shows an alternate "heat map" view, where each UI component that may be actuated by the user of the patient device is shown with an overlay, showing a heat map or graphical comparative view of how frequently each of the UI components has been used during the last measuring interval. In FIG. 37b, graphical indications in the form of different sized circles are used to show relative usage statistics. The larger the circle, the more often that UI component has been used. If desired, numerical statistics can be displayed along with the graphical indications or in place of the graphical indications. Of course, other ways of graphically representing a heat map may also be employed.

Second, feedback may also be sent to an Internet-based aggregation server computer 74 (FIG. 34) in the cloud 72 where usage metric statistics are aggregated across many users. The aggregated data is then used to update the cognitive ability metrics for each of the UI components. In this way, the degree of difficulty of each UI component is fine-tuned based on usage statistics gathered over time. If desired, the aggregate data can be weighted and combined with usage data from the specific patient, to provide a blended cognitive ability metric.

These aggregated data are also used by the portal computer 55 when automatically configuring a "recommended" user interface configuration for a particular patient. To achieve this, the portal computer receives from the aggregation server computer a set of UI component templates, representing recommended customization configurations for each of the applications stored on the portal computer that can be pushed to a patient device. These templates are constructed using the aggregate usage statistics so that UI components are selected to be consistent with each of a plurality of different ability levels.

To compile the aggregated statistical data, no personal information about the patient except for the patient's current cognitive ability metric is transferred to the cloud. Thus aggregation essentially entails making findings such as UI component A was not used by persons of cognitive ability below level 3; UI component B was not used by persons of cognitive ability below level 5, etc.

Manner of Programming Aggregation Server Computer

The aggregation server computer is a networked computer or collection of integrated computers that communicate over a suitable network connection with the portal computer, or alternatively, directly with the patient device(s). The aggregation server computer has at least one processor and associated non-transient memory into which the program instructions are stored to cause the aggregation server computer to implement the functions described here.

An exemplary aggregation computer employs the following software architecture by which the processor of the portal computer is programmed to perform the functions described here. Of course, different architectures may also be employed.

Data Collection Software Agent

A "Data Collection" software agent kept always running inside the patient device. The Data Collection software logs on a local buffer all system announcements such as message, picture, video, activity, and also all user interaction such as touch, application selection, and scroll. Every log data point is time-stamped to reflect the exact time it took place. According to a customizable frequency rate, the new log data points are uploaded to the portal using a Log_API.

Log_API—

This method allows clients to send information logs to the server. This can be used to send any important/relevant information.

Params:

apikey: The APIKEY obtained with the /login method.

data JSON: An array containing one or more objects in the following format: {"message": "A sample message", //A message to be sent "event_time": 1380566627, //A unix timestamp representing the message creation time "level": "INFO"//Log level. Valid options are: INFO, DEBUG, WARNING and ERROR}

Log Examples

| ID | Saved on Portal ID | Time stamp | IP | Type | Detailed description | Original Event Time Stamp |
|---|---|---|---|---|---|---|
| 50574 | 142 | 2013-09-30 16:41:21 | 10.0.33.224 | info | New message received from [ Guru ] | 2013-09-30 16:40:38 |
| 50573 | 142 | 2013-09-30 16:39:36 | 10.0.33.224 | info | TAB: video -> calendar | 2013-09-30 16:38:04 |
| 50572 | 142 | 2013-09-30 16:39:36 | 10.0.33.224 | info | TAB: calendar -> video | 2013-09-30 16:37:21 |
| 50571 | 142 | 2013-09-30 16:39:36 | 10.0.33.224 | info | TTS: [ 12:37PM ] App: [header] | 2013-09-30 16:37:17 |
| 50570 | 142 | 2013-09-30 15:23:01 | 10.0.33.224 | info | TAB: message -> calendar | 2013-09-30 15:21:27 |
| 50569 | 142 | 2013-09-30 15:23:01 | 10.0.33.224 | info | TAB: calendar -> message | 2013-09-30 15:21:19 |
| 50568 | 142 | 2013-09-30 15:23:01 | 10.0.33.224 | info | SCROLL 0 | 2013-09-30 15:21:12 |
| 50567 | 142 | 2013-09-30 15:23:01 | 10.0.33.224 | info | TTS: [ Tomorrow at 1:25PM Lunch ] App: [calendar] | 2013-09-30 15:21:11 |

Sample Source Code for Data Collection Running on the Patient Device

```
public function log_events($key = "")
{
  if ($this->high_server_load( )) return FALSE;
  if ($this->input->server('REQUEST_METHOD') != "POST") {
    $this->output_json(NULL, 400);
    return FALSE;
  }
  $key = (!empty($key)) ? $key : $this->input->get('key');
  $data = $this->input->post('data');
  $auth = $this->api->login->load($key);
  if ($auth)
  {
    try
    {
      $data = json_decode($data, TRUE);
      if (!is_array($data)) {
        $this->output_json(NULL, 400);
        return FALSE;
      }
      foreach ($data as $event)
      {
        $event = LogEvent::create(array(
          'calendar_id' => $auth->calendar->id,
          'class' => $event['level'],
          'description' => $event['message'],
          'event_time' => date('Y-m-d H:i:s', $event['event_time']),
          'ip_address' => $this->input->server('REMOTE_ADDR')
        ));
        $this->output_json(array(
          'status' => "OK"
        ));
      }
      return TRUE;
    }
    catch (Exception $exception)
    {
      $this->manager->log->error("Exception on api log_event: " . $exception->getMessage( ));
```

```
      }
      $this->output_json(array(
        'status' => "ERROR"
      ));
    }
    else
    {
      $this->output_json(array(
        'status' => "CREDENTIALS_ERROR"
      ));
    }
  }
}
```

The aggregation server computer 74 is programmed to compute aggregate ability metrics across all applications and UI components, for each different ability metric employed by the system (e.g., cognitive ability metrics, physical ability metrics, etc.). To do this, the aggregation server is programmed to receive usage data packets sent from each portal computer participating in the aggregation service. The portal computers are each programmed to periodically send usage data packets containing information extracted from the feedback received from the patient device(s) communicating with that portal computer.

The usage data packet consists of one or more records each containing the following information:

Portal ID (unique designator for the sending portal computer)

Ability Metric Designation (whether the record represents cognitive ability, physical ability or some other ability dimension)

Current Ability of Patient (ability level for the patient from whom the data was collected)

UI Component ID (unique designator for the particular user interface component or application being reported in this record)

Reporting Interval (the time interval over which the portal computer collected the data)

Usage Count (the number of times the UI component or application was used by the patient during the Reporting Interval)

Note that the data packet does not contain any information disclosing the identity of the patient. All that is known about the patient is his or her currently assigned ability level.

The aggregation server computer extracts and stores the data from the data packets received. The data are thus accumulated for a plurality of portal computers, each potentially serving a plurality of different patients. Thus the data collected by the aggregation server represents a population of patients, indicating the degree of difficulty the population had in using each of the different UI components and applications. From the aggregated data the aggregation server computes usage statistics that are then sent back to the respective portal computers.

The usage statistics include, for example, aggregate (population-wide) metrics for each UI component and application. For example, these aggregate metrics might show, for example, that the UI component having ID number 512 was used by 90% of the population of patients who reported an ability level of 3, but by only 20% of the population of patients who reported an ability level of 2. The statistics generated in this fashion, can be sent back to the participating portal computers where they are used in ranking the UI components and applications for presentation to the family members or nursing staff when designing a UI configuration for a particular patient.

The usage statistics generated by the aggregation server computer represent how the UI components are each received and understood by a potentially wide population of varying ability levels. Each individual patient may have specific ability levels that differ from the population. For example, a particular patient may generally track fairly consistently with the ability level 3 population, but may idiosyncratically have a level 4 ability in using a particular UI component or application. The portal computer can take this fact into account, by also using the usage data collected from that patient and overriding specific UI component rankings from the population to match the specific patient's abilities. This may be accomplished by storing a table of UI component rankings for each patient within the data storage system 56 of the portal computer. Initially, all UI component rankings are assigned the values received from the aggregate population. However, as specific UI component rankings are overridden to match the particular patient's abilities, these values are overwritten to replace the aggregate data stored in the table for that patient. In this way, the portal computer is able to display UI component rankings for each of the UI components and applications, even if those have never been used by that patient before. Then, as experience is gained in how that patient reacts to a particular UI component, the table is updated so that it eventually reflects the unique idiosyncrasies of that patient.

The UI component rankings generated by the aggregate population data may also be used by the portal computer in establishing the ability level of a particular patient. This is done by systematically pushing UI components and applications to the patient device in gradually increasing levels of difficulty (based on aggregate ranking metrics) over time until it can be established which UI components or applications the patient is not making good use of (based on the feedback provided from the patient device). The patient's ability level may then be established as being equal to the maximum ability level at which the patient was consistently able to perform. The goal here is not to challenge the patient, but rather to establish a baseline where the patient is comfortable using the UI components and applications that have been selected.

Kit of UI Components

The kit of UI components 62, stored in the data storage system 56 of portal computer 55, provide overlapping, and somewhat redundant, functionality. For example, the most simple gestural command made by the patient might be "touch anywhere on the screen." A more advanced one to do the same thing might be to press a single button labeled with the function the button performs. Higher still would be a menu bar of tabbed choices, with no sub-levels (essentially a row of labeled buttons); higher still would be a menu that provides one layer down of submenu choices, etc.

Selecting from this kit of UI components, FIGS. 36a and 36b show how the portal may be used to customize the user experience on the patient device. As previously explained, FIGS. 36a and 36b represent an exemplary photo-viewing application that has been configured for different levels of ability.

To effect this user interface customization functionality, each application (in this case the photo-viewing application) includes a data structure, defined in the local memory of the patient device, that stores the state of all configurable user interface components. Examples of these components are shown in FIGS. 36a and 36b and include: "previous photo," "next photo," "go back," "slide show state," "header bar date-time presentation size," "reminders" and the like. It will be understood that these are just some examples of the user interface components that may be configured.

The states of these user interface configuration variables are changed by interaction with the application via the portal. Using the portal, the states of these variables may be changed, and when changed, they affect how the application performs when run on the patient device.

In addition to saving user interface state variables, the data structure associated with each application also stores data, captured in real time, recording each instance when a particular user interface feature is used by the patient while operating the patient device. In one embodiment, illustrated in FIGS. 35a and 35b, a counter is incremented and stored in the usage history portion of the data structure. Date and timestamp information may also be stored in the data structure, recording exactly when the user interface feature was used by the patient. In the illustrated embodiment, the incremented number represents the number of times a particular feature was accessed within a predefined (customizable) interval of time. As shown, a 30-day interval has been chosen. Thus "231.30" indicates that the "previous photo" button was activated 231 times in the last 30 days. The data captured in the usage history is sent as feedback information to the portal, and also to the cloud server which collects aggregate statistics, as will be more fully described. Collecting usage history information allows the portal to display to the family member or caregiver which features of each application the patient is able to use. Features that are never used can be switched off, as shown in FIG. 36b.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

APPENDIX

Exemplary computer program code run on the portal computer to retrieve settings from the portal computer database and send those settings to the patient device to configure the display of the patient device.

```
private function api_settings($etag = FALSE)
{
    //Retrieve system wide default settings from database.
    $guru = $this->manager->setting->all_items(1);
    //Retrieve institution wide default settings from database.
    $institution = $this->manager->setting->all_items($this->getCalendar( )->institution_id);
    //Retrieve a list of chosen applications that will be running on the device, from database.
    $chosen_apps = $this->getDisplay( )->chosen_apps;
    //Retrieve the time of the latest update on the display settings.
    $display_update = empty($this->getDisplay( )->update_at) ? NULL : $this->getDisplay( )->update_at->format('U');
    $calendar_update = empty($this->getCalendar( )->update_at) ? NULL : $this->getCalendar( )->update_at->format('U');
    //If true, instead of returning the settings, a hash will be generated using the previously acquired data.
    //This hash is used to determine if we send new data to the device or tell it to keep using cached ones.
    if ($etag)
        return $chosen_apps . $display_update . $calendar_update . implode(array_values($institution)) . $this->api_weather(TRUE);
    //Build an array that, later on, will be converted into a JSON object and served to the device.
    return array(
        //Info section
        'info' => array(
            //Institution name
            'institution' => $this->getCalendar( )->institution->profile->name,
            //Resident name
            'resident' => $this->getCalendar( )->profile->name,
            //Weather information (temperature/weather conditions)
            'weather' => $this->api_weather( ),
        ),
        //Display section
        'display' => array(
            //If the display has night mode enabled
            'has_night_mode' => (!empty($this->getCalendar( )->night_mode_start)),
            //Day sections
            'day_span' => array(
                //When day mode starts (hour)
                'start' => $this->getCalendar( )->day_mode_start,
                //When night mode starts (hour)
                'stop' => $this->getCalendar( )->night_mode_start,
                //When sleep mode starts (hour)
                'sleep' => $this->getCalendar( )->sleep_mode_start
            ),
            //General display settings (most found in the Display tab on the server):
            //If day sound is enabled
            'allow_day_sound' => (!empty($this->getCalendar( )->day_sound)),
            //If night sound is enabled
            'allow_night_sound' => (!empty($this->getCalendar( )->night_sound)),
            //Amount of time to wait before polling the server for new data
            'polling_timeout' => $institution['pooling_timeout'],
            //If TTS (Text-To-Speech) is enabled
            'tts_enabled' => (!empty($institution['tts_enabled'])) ? (!empty($this->getCalendar( )->tts_enabled)) : FALSE,
            //Amount of time to wait before querying the server for a new bundle update (if needed).
            'download_retry' => $institution['download_retry'],
            //Amount of time to wait before retry to download a new bundle in case of failure.
            'download_failure_retry' => $institution['download_failure_retry'],
            //Automatic reboot setting. The device will reboot every 'reboot_rate' time (in seconds).
            'reboot_rate' => $institution['reboot_rate'],
            //Automatic wifi restart setting. The device will restart the wifi every 'wifi_restart_rate' time (in seconds).
            'wifi_restart_rate' => $institution['wifi_restart_rate'],
            //Device log level. Can be used to define the level of debug the device will send to the server.
            'log_level' => $this->getCalendar( )->log_level,
            //If relative time is enabled for TTS sentences.
            'relative_time' => (bool) $this->getCalendar( )->relative_time,
            //If vertical scroll is enabled for the calendar application
            'vertical_scroll' => (bool) $this->getCalendar( )->vertical_scroll,
            //The font zoom level of the calendar application
            'font_zoom_level' => $this->getCalendar( )->font_zoom_level,
            //If (and for how log to wait before) the device will go back to the calendar application.
            'return_to_calendar' => $this->getCalendar( )->return_to_calendar,
            //If screen saver is enabled, and for how long to wait before it's displayed.
            'screen_saver' => $this->getCalendar( )->screen_saver,
            //If sound detection (clap feature) is enabled.
            'sound_detection' => (bool) $this->getCalendar( )->sound_detection,
            //If notifications are enabled (sound and/or popup)
            'notification' => $this->getCalendar( )->notification,
            //Determines if notifications will happen every hour or at specific times.
            'notification_intervals' => $this->getCalendar( )->notification_intervals,
```

```
        //If the 'notification_intervals' is set to specific times, this item will contain a list of the specific times
        //in which the notifications popup/sounds will be displayed to the user.
        'notification_time' => $this->getCalendar( )->notification_time
    ),
    //A list of applications that will be running on the device.
    'chosen_apps' => empty($chosen_apps) ? NULL : explode(',', $chosen_apps),
    );
}
```

What is claimed is:

1. A computer-implemented system for assisting persons of reduced cognitive or physical ability comprising:
   a patient device having a display, a processor coupled to the display, and a communication port;
   a portal computer that communicates with the patient device through the communication port;
   the portal computer having a processor and associated memory storing a plurality of user interface components according to a predefined data structure that associates a patient ability metric with each user interface component;
   the portal computer being programmed to present the plurality of user interface components to a user of the portal computer in a presentation arrangement based on the ability metric;
   the portal computer being programmed to allow the first user to select from the arranged presentation of user interface components at least one interface component and then to push said selected user interface component to the patient device,
   wherein the processor of the patient device is programmed to provide feedback data to the portal computer regarding the patient's ability to use the selected user interface component pushed to the patient device,
   wherein the portal computer is further programmed to report the feedback data to an aggregator computer that compiles statistics on user interface suitability for different levels of patient ability, and
   wherein the portal computer is programmed to update the patient ability metric associated with a user interface component based on user interface usage data collected and aggregated from a plurality of patients.

2. The computer-implemented system of claim 1 wherein the portal computer is programmed to present a plurality of applications to the first user of the portal computer; and
   wherein the portal computer is programmed to allow the first user to select at least one application and then to configure and push said application to the patient device to be run by the processor of the patient device.

3. The computer-implemented system of claim 1 wherein the portal computer is programmed to present a plurality of applications to the first user of the portal computer in a presentation arrangement based on the ability metric; and
   wherein the portal computer is programmed to allow the first user to select from the arranged presentation of applications at least one application and then to push said application to the patient device to be run by the processor of the patient device.

4. The computer-implemented system of claim 1 wherein the aggregator computer is in communication with the portal computer and programmed to supply said ability metrics to the portal computer.

5. The computer-implemented system of claim 1 wherein the aggregator computer is in communication with the portal computer and programmed to receive usage data from the portal computer, to compute ability metrics based on said usage data and to supply said computed ability metrics to the portal computer.

6. The computer-implemented system of claim 1 wherein the portal computer stores application programs adapted to be run on the patient device and wherein the portal computer is programmed to push selected ones of the stored applications to the patient device.

7. The computer-implemented system of claim 6 wherein the portal computer associates an ability metric with each of the stored application programs.

8. The computer-implemented system of claim 6 wherein the portal computer associates an ability metric with each of the stored application programs and presents those applications to the user of the portal computer in a presentation arrangement based on the ability metric.

9. The computer-implemented system of claim 1 wherein the ability metric is a cognitive ability metric.

10. The computer-implemented system of claim 1 wherein the ability metric is a physical ability metric.

11. The computer-implemented system of claim 1 wherein the portal computer automatically suggests user interface components to be pushed to the patient device, using knowledge of the patient's ability and using the ability metrics in formulating the suggestion.

12. The computer-implemented system of claim 1 wherein the portal computer automatically selects and pushes user interface components to the patient device, using knowledge of the patient's ability and using the ability metrics in making the selection.

13. The computer-implemented system of claim 1 wherein the portal computer communicates through the communication port of the patient device to effect remote control over the patient device.

14. The computer-implemented system of claim 1 wherein the portal computer stores application programs adapted to be run on the patient device selected from the group consisting of calendar, messages, picture viewing, video viewing, music, weather, audio chat and audio-video chat.

* * * * *